United States Patent
Ben-Ari et al.

(10) Patent No.: US 9,592,214 B2
(45) Date of Patent: *Mar. 14, 2017

(54) COMPOUNDS FOR THE TREATMENT OF AUTISM IN A BABY CHILD

(71) Applicants: INSERM (INSTITUT NATIONAL DE LA SANTE ET DE LA RECHERCHE MEDICALE), Paris (FR); UNIVERSITE D'AIX MARSEILLE, Marseille 07 (FR); CHU DE BREST, Brest (FR)

(72) Inventors: Yehezkel Ben-Ari, La Ciotat (FR); Diana Carolina Ferrari, Marseille (FR); Romain Nardou, Marseille (FR); Eric LeMonnier, Limoges (FR)

(73) Assignees: INSERM (INSTITUT NATIONAL DE LA SANTE ET DE LA RECHERCHE MEDICALE), Paris (FR); UNIVERSITE D'AIX MARSEILLE, Marseille (FR); CHU DE BREST, Brest (FR)

(*) Notice: Subject to any disclaimer, the term of this patent is extended or adjusted under 35 U.S.C. 154(b) by 0 days.

This patent is subject to a terminal disclaimer.

(21) Appl. No.: 14/087,244

(22) Filed: Nov. 22, 2013

(65) Prior Publication Data

US 2014/0080910 A1    Mar. 20, 2014

Related U.S. Application Data

(63) Continuation-in-part of application No. 13/522,372, filed as application No. PCT/EP2011/050394 on Jan. 31, 2011, now Pat. No. 9,415,028.

(30) Foreign Application Priority Data

Jan. 15, 2010    (EP) .................... 10305047

(51) Int. Cl.

| A61K 39/395 | (2006.01) |
|---|---|
| A61K 31/196 | (2006.01) |
| G01N 33/50 | (2006.01) |
| A61K 31/192 | (2006.01) |
| A61K 31/4035 | (2006.01) |
| A61K 31/549 | (2006.01) |
| A61K 31/635 | (2006.01) |
| A61K 31/713 | (2006.01) |

(52) U.S. Cl.
CPC .......... *A61K 31/196* (2013.01); *A61K 31/192* (2013.01); *A61K 31/4035* (2013.01); *A61K 31/549* (2013.01); *A61K 31/635* (2013.01); *A61K 31/713* (2013.01)

(58) Field of Classification Search
None
See application file for complete search history.

(56) References Cited

U.S. PATENT DOCUMENTS

| 3,985,777 | A | 10/1976 | Feit |
|---|---|---|---|
| 4,247,550 | A | 1/1981 | Feit et al. |
| 4,946,778 | A | 8/1990 | Ladner et al. |
| 7,282,519 | B2 | 10/2007 | Garvey et al. |
| 2006/0089350 | A1 | 4/2006 | Hochman et al. |
| 2007/0032410 | A1 | 2/2007 | Quay et al. |
| 2007/0155729 | A1 | 7/2007 | Morgan et al. |
| 2012/0004225 | A1 | 1/2012 | Wanaski et al. |

FOREIGN PATENT DOCUMENTS

| GB | 2207129 | 1/1989 |
|---|---|---|
| WO | 2006110187 A2 | 10/2006 |
| WO | 2009068668 A1 | 6/2009 |
| WO | 2009/097695 | 8/2009 |
| WO | 2009/114950 | 9/2009 |
| WO | 2010/085352 | 7/2010 |
| WO | 2010/132999 | 11/2010 |
| WO | 2011/086126 | 7/2011 |
| WO | 2012018635 A2 | 2/2012 |

OTHER PUBLICATIONS

Bradstreet, et al.; "Sprironolactone Might Be a Desirable Immunologic and Hormonal Intervention in Autism Spectrum Disorders"; Med. Hypothesis; Feb. 20, 2007, pp. 979-987.
Nardou, et al.; "Bumetanide, an NKCC1 antagonist, does not prevent formation of epileptogenic focus but blocks epileptic focus seizures in immature rat hippocampus"; vol. 101, Mar. 18, 2009; pp. 2878-2888.
International Search Report dated Mar. 4, 2011; corresponding the the PCT/EP2011/050394.
Tyzio et al., "Maternal oxytocin triggers a transient inhibitory switch in GABA signaling in the fetal brain during delivery", Science, 2006, vol. 314, pp. 1788-1792.
Tyzio et al., "Postnatal changes in somatic gamma-aminobutyric acid signalling in the rat hippocampus", European Journal of Neuroscience. 2008, vol. 27, pp. 2515-2528.
Marrosu et al., "Paradoxical reactions elicited by diazepam in children with classic autism", Functional Neurology, 1987, vol. II, No. 3, pp. 355-661.
Nardou et al., "Neuronal chloride accumulation and excitatory GABA underlie aggravation of neonatal epileptiform activities by phenobarbital", Brain, A Journal of Neurology, 2011, vol. 134, pp. 987-1002.
Ben Ari et al., "GABA: a pioneer transmitter that excites immature neurons and generates primitive oscillations", Physiological Reviews, 2007, vol. 87, pp. 1215-1284.
Ben Ari, "Excitatory actions of gaba during development: the nature of the nurture", Nature Reviews Neuroscience, 2002, vol. 3, pp. 728-739.
Gagnon et al., "Characterization of SPAK and OSR1, regulatory kinases of the Na-K-2Cl cotransporter", Molecular and Cellular Biology, 2006, vol. 26, No. 2, pp. 689-698.

(Continued)

*Primary Examiner* — Olga N Chernyshev
(74) *Attorney, Agent, or Firm* — Young & Thompson

(57) ABSTRACT

The invention relates to a compound which inhibits the importation of chloride into neurons or a compound which improve the outflow of chloride from neurons for use in the treatment of autism in a baby or a fetus in need thereof.

7 Claims, 4 Drawing Sheets

(56) References Cited

OTHER PUBLICATIONS

Guinchat et al., "Pre-, peri- and neonatal risk factors for autism", Acta Obstetricia et Gynecologica Scandinavica, 2012, vol. 91, pp. 287-300.

Hultman et al., "Perinatal risk factors for infantile autism", Epidemiology, 2002, vol. 13, pp. 417-423.

Khalilov et al., "In vitro formation of a secondary epileptogenic mirror focus by interhippocampal propagation of seizures", Nature Neuroscience, 2003, vol. 6, No. 10, pp. 1079-1085.

Khalilov et al., "Epileptogenic actions of GABA and fast oscillations in the developing hippocampus", Neuron, 2005, vol. 48, pp. 787-796.

Pobbe et al., "Oxytocin receptor knockout mice display deficits in the expression of autism-related behaviors", Hormones and Behavior, 2012, vol. 61, No. 3, pp. 436-444.

Spitzer et al., "Action potentials, calcium transients and the control of differentiation of excitable cells", Current Opinion in Neurobiology, 1994, vol. 4, pp. 70-77.

Erickson et al., "STX209 (Arbaclofen) for autism spectrum disorders: an 8-week open-label study," J Autism Dev Disord. Apr. 2014;44(4):958-64.

Velazquez et al., "Control by drugs of renal potassium handling," Annu. Rev. Pharmacol. Toxicol. 1986;26:293-309.

Nakamura et al., "Investigation of brain serotonergic dysfunction in high-functioning autism," Ann. Rep. Mitsubishi Pharma Res. Found. 2005 37: 191-197.

Li et al., "Propofol Facilitates Glutamatergic Transmission to Neurons of the Ventrolateral Preoptic Nucleus," Anesthesiology. Dec. 2009; 111(6): 1271-1278.

Belenky et al., "Cell-type distribution of chloride transporters in the rat suprachiasmatic nucleus," Neuroscience. Feb. 17, 2010; 165(4): 1519-37.

COMPOUNDS FOR THE TREATMENT OF AUTISM IN A BABY CHILD

FIELD OF INVENTION

The invention relates to a compound which inhibits the importation of chloride into neurons or a compound which improve the outflow of chloride from neurons for use in the treatment of autism in a baby or a fetus.

BACKGROUND OF INVENTION

Autism Spectrum Disorder (ASD) is a developmental disorder characterized by restricted interest and communication impairment generated by genetic and environmental factors. The delivery period is instrumental in the pathogenesis of autism with complications during delivery and/or cesarean sections enhancing its incidence (Hultman et al. Epidemiology 13, 417 (2002); Guinchat et al., Acta Obstetricia et Gynecologica Scandinavica 91, 287 (2012)). Also, alterations of oxytocin signals that trigger labor and are instrumental for communication notably parental/infant interactions favor autism (Pobbe et al. Hormones and Behavior 61, 436 (2012)). Yet, in spite of these observations, the properties of immature autistic neurons before and shortly after delivery are presently unknown.

Brain maturation is associated with a developmental sequential expression of voltage gated, receptor synapse driven channels and brain patterns (Spitzer et al., 1994; Ben Ari et al., 2007). The developmental shifts of the actions of the inhibitory transmitter GABA is but one example of these changes. Immature neurons have a higher intracellular chloride concentration $(Cl^-)_I$ than adults leading to paradoxical excitatory actions of GABA (Ben Ari et al., Nat Rev Neurosci. 2002 September; 3(9):728-39; Ben Ari et al., Physiol Rev. 2007 October; 87(4):1215-84). This is due to an early expression of the co-transporter NKCC1 that imports chloride and a late operation of KCC2 that export chloride form neurons (Ben Ari et al., Nat Rev Neurosci. 2002 September; 3(9):728-39). In addition, the regulation of $(Cl^-)_I$ is dynamic and altered by even brief episodes of enhanced activity and more persistently by a variety of insults, lesions, seizures and neurological disorders (Khalilov I et al. (2003) Nat Neurosci 6:1079-1085; Khalilov I et al. (2005) 48:787-796).

The applicant already disclosed the use of NKCC inhibitors for the treatment of autism in children (WO2011/086126) but surprisingly, the inventors also discovered that treating a fetus before delivery or a baby could also treat ASD.

Indeed, the applicant characterized for the first time the cellular and network alterations that occur during the transition from fetal to post natal life and subsequently in an animal model of autism: the Valproate in utero model (VPA). The applicants' results stress the importance of events during delivery in the pathogenesis of autism and suggest that early diagnosis combined with the treatment with a modulator of chloride importation will be instrumental in preventing the deleterious cycle leading to autism.

SUMMARY

One object of the invention is a method for treating a subject presenting Autistic Syndrome Disorders (ASD), wherein said method comprises the administration of an effective amount of a modulator of a chloride transporter and wherein said subject is a human embryo, a human fetus, a new born child or a young child.

In one embodiment, said modulator is an inhibitor of a transporter involved in the importation of chloride into neurons.

In another embodiment, said modulator is an inhibitor of the expression of a transporter involved in the importation of chloride into neurons, preferably is siRNAs, shRNAs, antisense oligonucleotide, ribozymes or aptamers of a chloride transporter involved in the importation of chloride into neurons.

In another embodiment, said modulator is an inhibitor of the activity of a transporter involved in the importation of chloride into neurons.

In another embodiment, said modulator is an inhibitor of the transporter NKCC, preferably NKCC1.

In another embodiment, said modulator is an inhibitor of the transporter NKCC selected from the group comprising bumetanide, furosemide, ethacrynic acid, torsemide, azosemide, muzolimine, piretanide, tripamide and analogs, functional derivatives and/or prodrugs thereof thiazide and thiazide-like diuretics, such as bendroflumethiazide, benzthiazide, chlorothiazide, hydrochlorothiazide, hydro-flumethiazide, methylclothiazide, polythiazide, trichlormethiazide, chlorthalidone, indapamide, metolazone and quinethazone; analogs and/or functional derivatives and/or prodrugs thereof.

In another embodiment, the effective amount ranges from about 0.01 mg to about 500 mg.

In another embodiment, the modulator of a chloride transporter is administered directly to the subject in need thereof by subcutaneous, intramuscular, intravenous, intraocular, transdermal, topical, parenteral, intranasal and oral administration, or injection.

In another embodiment, the modulator of a chloride transporter is administered perinatally to the subject.

In another embodiment, the modulator of a chloride transporter is administered to a pregnant woman by subcutaneous, intramuscular, intravenous, intraocular, transdermal, topical, parenteral, intranasal and oral administration, or injection, preferably in utero.

In another embodiment, the subject suffered from complications delivery.

In another embodiment, the subject is at risk of developing ASD.

In another embodiment, the subject is diagnosed with ASD.

Another object is a method for treating Autistic Syndrome Disorders (ASD) in a subject in need thereof, wherein the chloride importation within neurons is inhibited in the subject, the subject being a human embryo, a human fetus, a new born child or a young child.

DEFINITIONS

In the present invention, the following terms have the following meanings:

"Mutation" refers to a stable change in the genomic sequence. Examples of mutation include, but are not limited to, point mutations, insertions, inversions, deletions within exons or flanking sequences, or gene rearrangements such as deletions, inversion or duplications of exons. In one embodiment, said mutation is a homozygote mutation. In another embodiment, said mutation is a heterozygote mutation.

"Treatment" refers to both therapeutic treatment and prophylactic or preventative measures; wherein the object is to prevent or slow down (lessen) the targeted pathologic condition or disorder. Those in need of treatment include those already with the disorder as well as those prone to have the disorder or those in whom the disorder is to be prevented. A subject is successfully "treated" for ASD if, after receiving an effective amount of a modulator according to the present invention, the subject shows observable and/or measurable reduction in or absence of one or more of the following: reduction in one or more of the symptoms associated with the ASD; and improvement in quality of life issues. The above parameters for assessing successful treatment and improvement in the disease are readily measurable by routine procedures familiar to a physician.

"Effective amount" refers to the level or amount of agent that is aimed at, without causing significant negative or adverse side effects to the target, (1) delaying or preventing the onset of ASD; (2) slowing down or stopping the progression, aggravation, or deterioration of one or more symptoms of ASD; (3) bringing about ameliorations of the symptoms of ASD; (4) reducing the severity or incidence of ASD; or (5) curing ASD. An effective amount may be administered prior to the onset of ASD, for a prophylactic or preventive action. Alternatively or additionally, the effective amount may be administered after initiation of ASD, for a therapeutic action.

"Subject" refers to a mammal, preferably a human.

—In one embodiment, the term "healthy subject" refers to a subject not diagnosed with ASD. In another embodiment, a healthy subject does not present symptoms and/or clinical signs of ASD.

"Modulator" refers to a compound that modulates intracellular chloride level. Preferably, a modulator is a compound whose administration leads to a decrease of intracellular chloride concentration. In one embodiment, said modulator acts on the ene and/or protein expression and/or on the activity of a chloride transporter.

"Selective modulator" refers to a selective inhibitor and a selective activator.

"Inhibitor" refers to refers to a natural or synthetic compound that has a biological effect to inhibit or significantly reduce or down-regulate the expression of a gene and/or a protein or that has a biological effect to inhibit or significantly reduce the biological activity of a protein. Consequently, "a NKCC inhibitor" refers to a natural or synthetic compound that has a biological effect to inhibit or significantly reduce or down-regulate the expression of the gene encoding for NKCC and/or the expression of the NKCC protein and/or the biological activity of NKCC.

"Selective inhibitor" refers to that the affinity of the inhibitor for the chloride transporter for instance NKCC is at least 10-fold, 25-fold, 50-fold, 75-fold, 80-fold, 90-fold, 95 fold, 100-fold, 125-fold, 150-fold, 200-fold, 250-fold, 300-fold, 350-fold, 400-fold, 450-fold, preferably 500-fold higher than the affinity for the other chloride transporters in particular KCC2.

"Activator" refers to a natural or synthetic compound which binds to the protein and stimulates the expression of a gene and/or a protein or that has a biological effect to stimulate the biological activity of a protein. Consequently, "a KCC activator" refers to a natural or synthetic compound that has a biological effect to stimulate the expression of the gene encoding for KCC and/or the expression of the KCC protein and/or the biological activity of KCC. The activator usually mimics the action of a natural activator that binds to the transcription factor.

"Selective activator" refers to that the affinity of the activator for the chloride transporter for instance KCC2 is at least 10-fold, 25-fold, 50-fold, 75-fold, 80-fold, 90-fold, 95 fold, 100-fold, 125-fold, 150-fold, 200-fold, 250-fold, 300-fold, 350-fold, 400-fold, 450-fold, preferably 500-fold higher than the affinity for the other chloride transporters such as NKCC1.

"About": preceding a figure means plus or less 10% of the value of said figure.

"Analog" refers broadly to the modification or substitution of one or more chemical moieties on a parent compound and may include functional derivatives, positional isomers, tautomers, zwitterions, enantiomers, diastereomers, racemates, isosteres or stereochemical mixtures thereof.

"Functional derivative" refers to a compound which possesses the capacity to modulate the concentration of chloride into neurons (inhibits the importation or activates the outflow of chloride).

DETAILED DESCRIPTION

This invention relates to a method for treating a subject presenting Autistic Syndrome Disorders (ASD), wherein said method comprises the administration of an effective amount of a modulator of a chloride transporter and wherein said subject is a human embryo, a human fetus or new born child.

In one embodiment of the invention, the modulator of intracellular chloride concentration is a modulator of a chloride transporter.

In one embodiment of the invention, the modulator of intracellular chloride concentration is a selective modulator of a chloride transporter.

In one embodiment, the modulator of a chloride transporter inhibits the importation of chloride into neurons, preferably through the inhibition of transporters involved in the importation of chloride into neurons.

In another embodiment, the selective modulator of a chloride transporter inhibits the importation of chloride into neurons, preferably through the inhibition of transporters involved in the importation of chloride into neurons.

In one embodiment of the invention, said modulator is an inhibitor of the chloride transporter involved in the importation of chloride into neurons.

In another embodiment of the invention, said modulator is a selective inhibitor of the chloride transporter involved in the importation of chloride into neurons.

In one embodiment of the invention, said modulator is an inhibitor of the protein and/or gene expression of a transporter involved in the importation of chloride into neurons.

In another embodiment of the invention, said modulator is a selective inhibitor of the protein and/or gene expression of a transporter involved in the importation of chloride into neurons.

Examples of transporters involved in the importation of chloride into neurons include, but are not limited to, NKCC (wherein NKCC stands for "Na—K-2Cl co-transporter"), such as, for example, NKCC1. In one embodiment, the modulator of a chloride transporter is thus an inhibitor of NKCC, preferably of NKCC1. In another embodiment, the modulator of a chloride transporter is a selective inhibitor of NKCC, preferably of NKCC1.

In one embodiment of the invention, the inhibitor of a chloride transporter inhibits the expression of said chloride transporter. Examples of inhibitors of the expression of a chloride transporter include, but are not limited to, siRNAs, shRNAs, anti-sense oligonucleotide, ribozymes or aptamers of a chloride transporter.

In another embodiment of the invention, the selective inhibitor of a chloride transporter is an aptamer. Aptamers are a class of molecule that represents an alternative to antibodies in term of molecular recognition. Aptamers are oligonucleotide or oligopeptide sequences with the capacity to recognize virtually any class of target molecules with high affinity and specificity. Such ligands may be isolated through Systematic Evolution of Ligands by EXponential enrichment (SELEX) of a random sequence library, as described in Tuerk C. and Gold L., 1990. The random sequence library is obtainable by combinatorial chemical synthesis of DNA. In this library, each member is a linear oligomer, eventually chemically modified, of a unique sequence. Possible modifications, uses and advantages of this class of molecules have been reviewed in Jayasena S. D., 1999. Peptide aptamers consists of a conformationally constrained antibody variable region displayed by a platform protein, such as E. coli Thioredoxin A that are selected from combinatorial libraries by two hybrid methods (Colas et al., 1996).

Then after raising aptamers directed against the chloride transporter as above described, the skilled man in the art can easily select those blocking chloride importation. Inhibitors of chloride transporter gene expression for use in the present invention may be based on anti-sense oligonucleotide constructs. Anti-sense oligonucleotides, including anti-sense RNA molecules and anti-sense DNA molecules, would act to directly block the translation of chloride transporter mRNA by binding thereto and thus preventing protein translation or increasing mRNA degradation, thus decreasing the level of chloride transporter, and thus activity, in a cell. For example, anti-sense oligonucleotides of at least about 15 bases and complementary to unique regions of the mRNA transcript sequence encoding chloride transporter can be synthesized, e.g., by conventional phosphodiester techniques and administered by e.g., intravenous injection or infusion. Methods for using antisense techniques for specifically inhibiting gene expression of genes whose sequence is known are well known in the art (e.g. see U.S. Pat. Nos. 6,566,135; 6,566,131; 6,365,354; 6,410,323; 6,107,091; 6,046,321; and 5,981,732).

Small inhibitory RNAs (siRNAs) can also function as inhibitors of chloride transporter gene expression for use in the present invention. Chloride transporter gene expression can be reduced by contacting a subject or cell with a small double stranded RNA (dsRNA), or a vector or construct causing the production of a small double stranded RNA, such that chloride transporter gene expression is specifically inhibited (i.e. RNA interference or RNAi). Methods for selecting an appropriate dsRNA or dsRNA-encoding vector are well known in the art for genes whose sequence is known (e.g. see Tuschl, T. et al. (1999); Elbashir, S. M. et al. (2001); Hannon, G J. (2002); McManus, M T. et al. (2002); Brummelkamp, T R. et al. (2002); U.S. Pat. Nos. 6,573,099 and 6,506,559; and International Patent Publication Nos. WO 01/36646, WO 99/32619, and WO 01/68836).

Ribozymes can also function as inhibitors of chloride transporter gene expression for use in the present invention. Ribozymes are enzymatic RNA molecules capable of catalyzing the specific cleavage of RNA. The mechanism of ribozyme action involves sequence specific hybridization of the ribozyme molecule to complementary target RNA, followed by endonucleolytic cleavage. Engineered hairpin or hammerhead motif ribozyme molecules that specifically and efficiently catalyze endonucleolytic cleavage of chloride transporter mRNA sequences are thereby useful within the scope of the present invention. Specific ribozyme cleavage sites within any potential RNA target are initially identified by scanning the target molecule for ribozyme cleavage sites, which typically include the following sequences, GUA, GUU, and GUC. Once identified, short RNA sequences of between about 15 and 20 ribonucleotides corresponding to the region of the target gene containing the cleavage site can be evaluated for predicted structural features, such as secondary structure, that can render the oligonucleotide sequence unsuitable. The suitability of candidate targets can also be evaluated by testing their accessibility to hybridization with complementary oligonucleotides, using, e.g., ribonuclease protection assays.

Both antisense oligonucleotides and ribozymes useful as inhibitors of chloride transporter gene expression can be prepared by known methods. These include techniques for chemical synthesis such as, e.g., by solid phase phosphoramadite chemical synthesis. Alternatively, anti-sense RNA molecules can be generated by in vitro or in vivo transcription of DNA sequences encoding the RNA molecule. Such DNA sequences can be incorporated into a wide variety of vectors that incorporate suitable RNA polymerase promoters such as the T7 or SP6 polymerase promoters. Various modifications to the oligonucleotides of the invention can be introduced as a means of increasing intracellular stability and half-life. Possible modifications include but are not limited to the addition of flanking sequences of ribonucleotides or deoxyribonucleotides to the 5' and/or 3' ends of the molecule, or the use of phosphorothioate or 2'-O-methyl rather than phosphodiesterase linkages within the oligonucleotide backbone.

Antisense oligonucleotides siRNAs and ribozymes of the invention may be delivered in vivo alone or in association with a vector. In its broadest sense, a "vector" is any vehicle capable of facilitating the transfer of the antisense oligonucleotide siRNA or ribozyme nucleic acid to the cells and preferably cells expressing a chloride transporter. Preferably, the vector transports the nucleic acid to cells with reduced degradation relative to the extent of degradation that would result in the absence of the vector. In general, the vectors useful in the invention include, but are not limited to, plasmids, phagemids, viruses, other vehicles derived from viral or bacterial sources that have been manipulated by the insertion or incorporation of the antisense oligonucleotide siRNA or ribozyme nucleic acid sequences. Viral vectors are a preferred type of vector and include, but are not limited to nucleic acid sequences from the following viruses: retrovirus, such as moloney murine leukemia virus, harvey murine sarcoma virus, murine mammary tumor virus, and rouse sarcoma virus; adenovirus, adeno-associated virus; SV40-type viruses; polyoma viruses; Epstein-Barr viruses; papilloma viruses; herpes virus; vaccinia virus; polio virus; and RNA virus such as a retrovirus. One can readily employ other vectors not named but known to the art.

Preferred viral vectors are based on non-cytopathic eukaryotic viruses in which non-essential genes have been replaced with the gene of interest. Non-cytopathic viruses include retroviruses (e.g., lentivirus), the life cycle of which involves reverse transcription of genomic viral RNA into DNA with subsequent proviral integration into host cellular DNA. Retroviruses have been approved for human gene therapy trials. Most useful are those retroviruses that are replication-deficient (i.e., capable of directing synthesis of the desired proteins, but incapable of manufacturing an infectious particle). Such genetically altered retroviral expression vectors have general utility for the high-efficiency transduction of genes in vivo. Standard protocols for producing replication-deficient retroviruses (including the steps of incorporation of exogenous genetic material into a plasmid, transfection of a packaging cell lined with plasmid, production of recombinant retroviruses by the packaging cell line, collection of viral particles from tissue culture media, and infection of the target cells with viral particles) are provided in Kriegler, 1990 and in Murry, 1991).

Preferred viruses for certain applications are the adenoviruses and adeno-associated viruses, which are double-stranded DNA viruses that have already been approved for human use in gene therapy. The adeno-associated virus can be engineered to be replication deficient and is capable of infecting a wide range of cell types and species. It further has advantages such as, heat and lipid solvent stability; high transduction frequencies in cells of diverse lineages, including hemopoietic cells; and lack of superinfection inhibition thus allowing multiple series of transductions. Reportedly, the adeno-associated virus can integrate into human cellular DNA in a site-specific manner, thereby minimizing the possibility of insertional mutagenesis and variability of inserted gene expression characteristic of retroviral infection. In addition, wild-type adeno-associated virus infections have been followed in tissue culture for greater than 100 passages in the absence of selective pressure, implying that the adeno-associated virus genomic integration is a relatively stable event. The adeno-associated virus can also function in an extrachromosomal fashion.

Other vectors include plasmid vectors. Plasmid vectors have been extensively described in the art and are well known to those of skill in the art. See e.g. Sambrook et al., 1989. In the last few years, plasmid vectors have been used as DNA vaccines for delivering antigen-encoding genes to cells in vivo. They are particularly advantageous for this because they do not have the same safety concerns as with many of the viral vectors. These plasmids, however, having a promoter compatible with the host cell, can express a peptide from a gene operatively encoded within the plasmid. Some commonly used plasmids include pBR322, pUC18, pUC19, pRC/CMV, SV40, and pBlueScript. Other plasmids are well known to those of ordinary skill in the art. Additionally, plasmids may be custom designed using restriction enzymes and ligation reactions to remove and add specific fragments of DNA. Plasmids may be delivered by a variety of parenteral, mucosal and topical routes. For example, the DNA plasmid can be injected by intramuscular, intradermal, subcutaneous, or other routes. It may also be administered by intranasal sprays or drops, rectal suppository and orally. It may also be administered into the epidermis or a mucosal surface using a gene-gun. The plasmids may be given in an aqueous solution, dried onto gold particles or in association with another DNA delivery system including but not limited to liposomes, dendrimers, cochleate and microencapsulation.

In another embodiment, the inhibitor of a chloride transporter inhibits the activity of the chloride transporter. Examples of such inhibitors include, but are not limited to, small molecules, antibodies, minibodies, diabodies or fragments thereof binding to the chloride transporter, and antagonists of the chloride transporter.

In another embodiment, the inhibitor of the invention is an antibody (the term including antibody fragment) that can block the activity of a transporter involved in the importation of chloride into neurons.

In particular, the inhibitor of the invention may consist in an antibody directed against a transporter involved in the importation of chloride into neurons.

Antibodies directed against said transporter can be raised according to known methods by administering the appropriate antigen or epitope to a host animal selected, e.g., from pigs, cows, horses, rabbits, goats, sheep, and mice, among others. Various adjuvants known in the art can be used to enhance antibody production. Although antibodies useful in practicing the invention can be polyclonal, monoclonal antibodies are preferred. Monoclonal antibodies against said transporter can be prepared and isolated using any technique that provides for the production of antibody molecules by continuous cell lines in culture. Techniques for production and isolation include but are not limited to the hybridoma technique originally described by Kohler and Milstein (1975); the human B-cell hybridoma technique (Cote et al., 1983); and the EBV-hybridoma technique (Cole et al. 1985). Alternatively, techniques described for the production of single chain antibodies (see e.g. U.S. Pat. No. 4,946,778) can be adapted to produce anti-modulator, or anti-modulator ligands single chain antibodies. Chloride transporter inhibitor useful in practicing the present invention also include anti-modulator, or anti-modulator ligands antibody fragments including but not limited to $F(ab')_2$ fragments, which can be generated by pepsin digestion of an intact antibody molecule, and Fab fragments, which can be generated by reducing the disulfide bridges of the $F(ab')_2$ fragments. Alternatively, Fab and/or scFv expression libraries can be constructed to allow rapid identification of fragments having the desired specificity to said transporter.

In another embodiment, the inhibitor of the invention can include isomers, tautomers, zwitterions, enantiomers, diastereomers, racemates, or stereochemical mixtures thereof. Inhibitors of the present invention can also comprise isosteres.

The term "isosteres" as used herein broadly refers to elements, functional groups, substituents, molecules, or ions having different molecular formulae but exhibiting similar or identical physical properties. For example, tetrazole is an isostere of carboxylic acid because it mimics the properties of carboxylic acid even though they both have different molecular formulae. Typically, two isosteric molecules have similar or identical volumes and shapes. Other physical properties that isosteric compounds usually share include boiling point, density, viscosity, and thermal conductivity. However, certain properties are usually different: dipolar moments, polarity, polarization, size, and shape since the external orbitals may be hybridized differently.

The term "isomers" as used herein refers broadly to compounds having the same number and kind of atoms, and hence the same molecular weight, but differing with respect to the arrangement or configuration of the atoms in space. Additionally, the term "isomers" includes stereoisomers and geometric isomers. The terms "stereoisomer" or "optical isomer" as used herein refer to a stable isomer that has at least one chiral atom or restricted rotation giving rise to perpendicular dissymmetric planes (e.g., certain biphenyls, allenes, and spiro compounds) and can rotate plane-polarized light. Because asymmetric centers and other chemical structure can exist in some of the compounds of the present invention, which may give rise to stereoisomerism, the invention contemplates stereoisomers and mixtures thereof. The compounds of the present invention and their salts can include asymmetric carbon atoms and may therefore exist as single stereoisomers, racemates, and as mixtures of enantiomers and diastereomers. Typically, such compounds will be prepared as a racemic mixture. Such compounds can also be prepared or isolated as pure stereoisomers, i.e., as individual enantiomers or diastereomers, or as stereoisomer-enriched mixtures. Tautomers are readily inter-convertible constitutional isomers and there is a change in connectivity of a ligand, as in the keto and enol forms of ethyl acetoacetate (including tautomers of any said compounds.) Zwitterions are inner salts or dipolar compounds possessing acidic and basic groups in the same molecule. At neutral pH, the cation and anion of most zwitterions are equally ionized.

Examples of such inhibitors include, but are not limited to, NKCC inhibitors, such as, for example, NKCC antagonists. In one embodiment, the modulator is an antagonist of NKCC1. In one embodiment, said inhibitor is a selective NKCC inhibitor, preferably a selective NKCC1 inhibitor.

In one embodiment of the invention, said selective inhibitor interacts directly with the chloride transporter.

In one embodiment, said selective inhibitor is an antagonist of a chloride transporter importing chloride into neurons.

In one embodiment of the invention, the inhibitor of a chloride transporter is an inhibitor of NKCC1, such as, for example, a diuretic (such as, for example, a loop diuretic); or a NKKC1 antagonist.

In one embodiment of the invention, the selective inhibitor decreasing the gene and/or protein expression and/or activity of the chloride co-transporter NKCC1, has a low affinity for KCC2.

In one embodiment of the invention, the selective inhibitor of the chloride transporter has an affinity for KCC2 inferior than $10^{-7}$ M, preferably $10^{-6}$ M, more preferably less than $10^{-5}$ M.

In another embodiment of the invention, the selective inhibitor of the chloride transporter has an affinity at least much higher to NKCC1 than to KCC2 (of at least 2 orders of magnitude, preferably of at least 4 orders of magnitude, more preferably of at least 5 orders of magnitude and most preferably of at least 6 orders of magnitude higher binding constant (at least $10^{-9}$, preferably more than $10^{-10}$).

In another embodiment of the invention, the selective inhibitor of the chloride transporter does not bind to KCC2 at all.

In one embodiment of the invention, the selective inhibitor of the chloride transporter refers to a molecule that has an affinity for the NKCC1 at least 10-fold, 25-fold, 50-fold, 75-fold, 80-fold, 90-fold, 95 fold, 100-fold, 125-fold, 150-fold, 200-fold, 250-fold, 300-fold, 350-fold, 400-fold, 450-fold, preferably 500-fold higher than its affinity for any one of other isoforms of NKCC transporters comprising NKCC2, KCC transporters comprising KCC1, KCC2, KCC3, KCC4, other transporter chloride including in a non-limiting list: Cl$^-$HCO3$^-$ transporter.

Examples of inhibitors of a chloride transporter, preferably of NKCC1, include, but are not limited to, bumetanide, furosemide, ethacrynic acid, torsemide, azosemide, muzolimine, piretanide, tripamide and analogs, functional derivatives and prodrugs of such compounds; thiazide and thiazide-like diuretics, such as bendroflumethiazide, benzthiazide, chlorothiazide, hydrochlorothiazide, hydro-flumethiazide, methylclothiazide, polythiazide, trichlormethiazide, chlorthalidone, indapamide, metolazone and quinethazone; and analogs, functional derivatives and prodrugs of such compounds.

Examples of analogs of bumetanide include, but are not limited to: bumetanide aldehyde, bumetanide dibenzylamide, bumetanide diethylamide, bumetanide morpholinoethyl ester, bumetanide 3-(dimethylaminopropyl) ester, bumetanide N,N-diethylglycolamide ester, bumetanide dimethylglycolamide ester, bumetanide pivaxetil ester, bumetanide methoxy(polyethyleneoxy)$_{n-1}$-ethyl ester, bumetanide benzyltrimethyl-ammonium salt, bumetanide cetyltrimethylammonium salt, pivaloyloxymethyl ester of bumetanide, methyl ester of bumetanide, N,N-dimethylaminoethyl ester of bumetanide, bumetanide [—(C═O)—SH] thioacid, bumetanide S-methyl thioester, bumetanide S-cyanotnethyl thioester, bumetanide S-ethyl thioester, bumetanide S-isoamyl thioester, bumetanide S-octyl thioester, bumetanide S-benzyl thioester, bumetanide S-(morpholinoethyl) thioester, bumetanide S-[3-(dimethylaminopropyl)] thioester, bumetanide S—(N,N-diethylglycolamido) thioester, bumetanide S—(N,N-dimethylglycolamido) thioester, bumetanide S-pivaxetil thioester, bumetanide S-propaxetil thioester, bumetanide S-(methoxyipolyethyleneoxy)$_{n-1}$-ethyl] thioester, bumetanide [—(C═O)—S$^-$] benzyltrimethyl-ammonium thioacid salt and bumetanide [—(C═O)—S] cetyltrimethylammonium thioacid salt; metast-able bumetanide thioacid, bumetanide thioaldehyde, bumetanide O-methyl thioester, bumetanide O-cyanomethyl thioester, bumetanide O-ethyl thioester, bumetanide O-isoamyl thioester, bumetanide O-octyl thioester, bumetanide O-benzyl thioester, bumetanide O-(morpholinoethyl) thioester, bumetanide O-[3-(dimethylaminopropyl)J thioester, bumetanide O—(N,N-diethylglycolamido) thioester, bumetanide O-pivaxetil thioester, bumetanide O-propaxetil thioester, bumetanide O-[methoxy(poryethyleneoxy)$_{n-1}$ ethyl] thioester, bumetanide [—(C═S)—O$^-$] benzyltrimemyl-ammonium thioacid salt and bumetanide [—(C═S)—O$^-$] cetyltrimethylammonium thioacid salt.

Examples of analogs of furosemide include, but are not limited to: furosemide aldehyde, furosemide ethyl ester, furosemide cyanomethyl ester, furosemide benzyl ester, furosemide morpholinoethyl ester, furosemide 3-(dimethylaminopropyl) ester, furosemide N,N-diethylglycolamide ester, furosemide dibenzylamide, furosemide benzyltrimethylammonium salt, furosemide cetyltrimethylammonium salt, furosemide N,N-dimethylglycolamide ester, furosemide methoxy(polyethyleneoxy)$_{n-1}$-ethyl ester, furosemide pivaxetil ester, furosemide propaxetil ester, furosemide benzyltrimethylammonium acid salt and furosemide cetyltrimethylammonium acid salt, furosemide [—(C═O)—SH] thioacid, furosemide S-methyl thioester, furosemide S-cyanomethyl thioester, furosemide S-ethyl thioester, furosemide S-isoamyl thioester, furosemide S-octyl thioester, furosemide S-benzyl thioester, furosemide S-(morpholinoethyl) thioester, furosemide S-[3-(dimethylaminopropyl)] thioester, furosemide S—(N,N-diethylglycolamido) thioester, furosemide S—(N,N-dimethylglycolamido) thioester, furosemide S-pivaxetil thioester, furosemide S-propaxetil thioester, furosemide S-[methoxy(polyethyleneoxy)$_{n-1}$-ethyl] thioester, furosemide [—(C═O)—S$^-$] benzyltrimethylammonium thioacid salt and furosemide [—(C═O)—S$^-$] cetyltrimethylammonium thioacid salt, metasta-stable furosemide [—(C═S)—OH] thioacid, furosemide O-methyl thioester, furosemide O-cyanomethyl thioester, furosemide O-ethyl thioester, furosemide O-isoamyl thioester, furosemide O-octyl thioester, furosemide O-benzyl thioester, furosemide O-(morpholinoethyl) thioester, furosemide O-[3-(dimethylaminopropyl)] thioester, furosemide O—(N,N-diethylglycolamido) thioester, furosemide O—(N,N-dimethylglycolamido) thioester, furosemide O-pivaxetil thioester, furosemide O-propaxetil thioester, furosemide O-[methoxy(polyethyleneoxy)$_{n-1}$-ethyl]thioester, furosemide [—(C═S)—O$^-$] benzyltrimethyl-ammonium thioacid salt and furosemide [—(C=S)—O⁻] cetyltrimethylammonium thioacid salt; furosemide thioaldehyde, furosemide [—(C=S)—SH] dithioacid, furosemide methyl dithioester, furosemide cyanomethyl dithioester, furosemide ethyl dithioester, furosemide isoamyl dithioester, furosemide octyl dithioester, furosemide benzyl dithioester, furosemide dibenzyl-thioamide, furosemide diethylthioamide, furosemide morpholinoethyl dithioester, furosemide 3-(dimethylaminopropyl) dithioester, furosemide N,N-diethylglycolamido dithioester, furosemide N,N-dimethylglycolamido dithioester, furosemide pivaxetil dithioester, furosemide propaxetil dithioester, furosemide methoxy(polyethyleneoxy)$_{n-1}$ ethyl dithioester, furosemide benzyltrimethylammonium dithioacid salt and furosemide cetyltrimethylammonium dithioacid salt.

Examples of analogs of piretanide include, but are not limited to: piretanide aldehyde, piretanide methyl ester, piretanide cyanomethyl ester, piretanide benzyl ester, piretanide morpholinoethyl ester, piretanide 3-(dimethylaminopropyl) ester, piretanide N,N-diethylglycolamide ester, piretanide diethylamide, piretanide dibenzylamide, piretanide benzylltrimethylammonium salt, piretanide cetylltrimethylamrnonium salt, piretanide N,N-dimethylglycolamide ester, piretanide methoxy(polyethyleneoxy)$_{n-1}$-ethyl ester, piretanide pivaxetil ester, piretanide propaxetil ester, piretanide [—(C=O)—SH] thioacid, piretanide S-methyl thioester, piretanide S-cyanomethyl thioester, piretanide S-ethyl thioester, piretanide S-isoamyl thioester, piretanide S-octyl thioester, piretanide S-benzyl thioester, piretanide S-(morpholinoethyl) thioester, piretanide S-[3-(dimethylaminopropyl)] thioester, piretanide S—(N,N-diethylglycolamido) thioester, piretanide S—(N,N-dimethylglycolamido) thioester, piretanide S-pivaxetil thioester, piretanide S-propaxetil thioester, piretanide S-[methoxy(polyethyleneoxy)$_{n-1}$ ethyl] thioester, piretanide [—(C=O)—S⁻] benzyltrimethylammonium thioacid salt and piretanide [—(C=O)—S⁻] cetyltrimethylammonium thioacid salt; metastable piretanide [—(C=S)—OH] thioacid, piretanide O-methyl thioester, piretanide O-cyanomethyl thioester, piretanide O-ethyl thioester, piretanide O-isoamyl thioester, piretanide O-octyl thioester, piretanide O-benzyl thioester, piretanide O-(morpholinoethyl) thioester, piretanide O-[3-(dimethylaminopropyl)] thioester, piretanide O—(N,N-diethylglycolamido) thioester, piretanide, O—(N,N-dimethylglycolamido) thioester, piretanide O-pivaxetil thioester, piretanide O-propaxetil thioester, piretanide O-[methoxy(polyethyleneoxy)$_{n-1}$ ethyl] thioester, piretanide [—(C=S)—O⁻] benzyltrimethylammonium thioacid salt and piretanide [—(C=S)—O⁻] cetyltrimethylammonium thioacid salt; piretanide thioaldehyde, piretanide [—(C=S)—SH] dithioacid, piretanide methyl dithioester, piretanide cyanomethyl dithioester, piretanide ethyl dithioester, piretanide isoamyl dithioester, piretanide octyl dithioester, piretanide benzyl dithioester, piretanide dibenzylthioamide, piretanide diethyl-thioamide, piretanide morpholinoethyl dithioester, piretanide 3-(dimethylaminopropyl) di-thioester, piretanide N,N-diethylglycolamido dithioester, piretanide N,N-dimethylglycolamido dithioester, piretanide pivaxetil dithioester, piretanide propaxetil dithioester, piretanide methoxytpolyethyleneoxyLr-ethyl dithioester, piretanide benzyl-trimethylammonium dithioacid salt and piretanide cetyltrimethylammoniurn dithioacid salt.

Examples analogs of azozemide and include, but are not limited to: tetrazolyl-substituted azosemides (such as methoxymethyl tetrazolyl-substituted azosemides, methylthiomethyl tetrazolyl-substituted azosemides, N-mPEG350-tetrazolyl-substituted azosemides), azosemide benzyltrimethylammoniurn salt, azosemide cetyltrimethylammonium salt, pyridine-substituted torsemide quaternary ammonium salts or the corresponding inner salts (zwitterions), methoxymethylpyridinium torsemide salts, methylthiomethylpyridinium torsemide salts and N-mPEG350-pyridinium torsemide salts.

In another embodiment, an analog of an inhibitor according to the invention may have a formula as described in the patent application WO2006/110187. Examples of said analogs include, but are not limited to, compounds of general formula I, II and/or III:

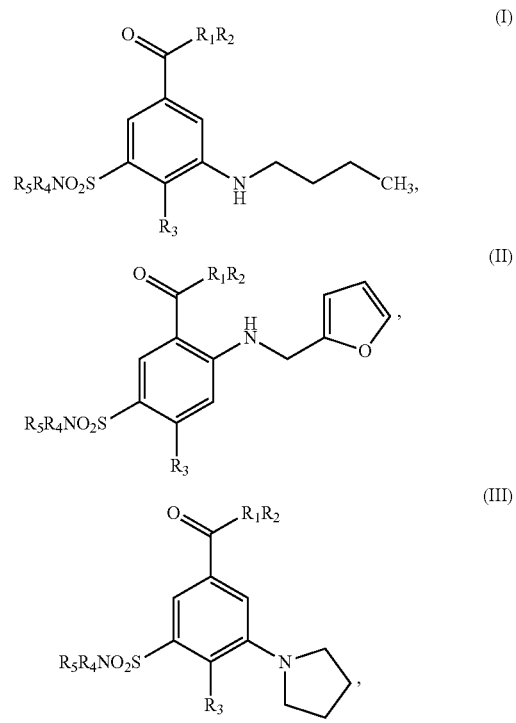

or a pharmaceutically acceptable salt, solvate, tautomer or hydrate thereof, wherein
- —R1 is not present, H or O;
- R2 is H or when R1 is O, is selected from the group consisting of: alkylaminodialkyl, alkylaminocarbonyldialkyl, alkyloxycarbonylalkyl, alkylaldehyde, alkylketoalkyl, alkylamide, an alkylammonium group, alkylcarboxylic acid, alkylheteroaryls, alkylhydroxy, a biocompatible polymer such as alkyloxy(polyalkyloxy) alkylhydroxyl, a polyethylene glycol (PEG), a polyethylene glycol ester (PEG ester), a polyethylene glycol ether (PEG ether), methyloxyalkyl, methyloxyalkaryl, methylthioalkylalkyl and methylthioalkaryl, unsubstituted or substituted, and when R1 is not present, R2 is selected from the group consisting of: hydrogen, dialkylamino, diarylamino, dialkylaminodialkyl, dialkylcarbonylaminodialkyl, dialkylesteralkyl, dialkylaldehyde, dialkylketoalkyl, dialkylamido, dialkylcarboxylic acid, and dialkylheteroaryls, unsubstituted or substituted;
- R3 is selected from the group consisting of: aryl, halo, hydroxy, alkoxy, and aryloxy, unsubstituted or substituted; and
- R4 and R5 are each independently selected from the group consisting of: hydrogen, alkylaminodialkyl, alkylhydroxyaminodiakyl, unsubstituted or substituted.

Another non-limiting example of said analogs of an inhibitor of the invention is a compound of general formula IV

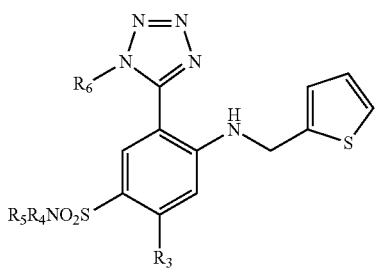

(IV)

or a pharmaceutically acceptable salt, solvate, tautomer or hydrate thereof, wherein R3, R4 and R5 are as defined above; and R6 is selected from the group consisting of: alkyloxycarbonylalkyl, alkylaminocarbonyldialkyl, alkylaminodialkyl, alkylhydroxy, a biocompatible polymer such as alkyloxy(polyalkyloxy)alkylhydroxyl, a polyethylene glycol (PEG), a polyethylene glycol ester (PEG ester), a polyethylene glycol ether (PEG ether), methyloxyalkyl, methyloxyalkaryl, methylthioalkyl and methylthioalkaryl, unsubstituted or substituted.

Another non-limiting example of said analogs is a compound of general formula V

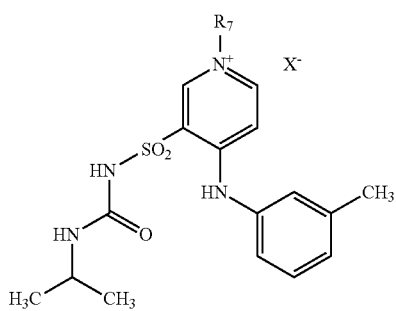

(V)

or a pharmaceutically acceptable salt, solvate, tautomer or hydrate thereof, wherein R7 is selected from the group consisting of: alkyloxycarbonylalkyl, alkylaminocarbonyldialkyl, alkylaminodialkyl, alkylhydroxy, a biocompatible polymer such as alkyloxy(polyalkyloxy)alkylhydroxyl, a polyethylene glycol (PEG), a polyethylene glycol ester (PEG ester), a polyethylene glycol ether (PEG ether), methyloxyalkyl, methyloxyalkaryl, methylthioalkyl and methylthioalkaryl, unsubstituted or substituted; and $X^-$ is a halide such as bromide, chloride, fluoride, iodide or an anionic moiety such as mesylate or tosylate; alternatively, $X^-$ is not present and the compound forms an "inner" or zwitterionic salt by loss of a proton from the sulfonylurea moiety (—SO2-NH—CO—).

The term "alkyl" as used herein refers to a straight or branched chain saturated or partially unsaturated hydrocarbon radical, wherein by "unsaturated" is meant the presence of 1, 2 or 3 double or triple bonds, or a combination thereof. Examples of alkyl groups include, but are not limited to, methyl, ethyl, isopropyl, tert-butyl, n-pentyl and the like.

The term "alkylene" as used herein refers to a straight or branched chain having two terminal monovalent radical centers derived by the removal of one hydrogen atom from each of the two terminal carbon atoms of straight-chain parent alkane.

The term "aryl" as used herein refers to an aromatic group or to an optionally substituted aromatic group fused to one or more optionally substituted aromatic groups, optionally substituted with suitable substituents including, but not limited to, lower alkyl, lower alkoxy, lower alkylsulfanyl, lower alkylsulfenyl, lower alkylsulfonyl, oxo, hydroxy, mercapto, amino optionally substituted by alkyl, carboxy, tetrazolyl, carbamoyl optionally substituted by alkyl, aminosulfonyl optionally substituted by alkyl, acyl, aroyl, heteroaroyl, acyloxy, aroyloxy, heteroaroyloxy, alkoxycarbonyl, nitro, cyano, halogen, or lower perfluoroalkyl, multiple degrees of substitution being allowed. Examples of aryl include, but are not limited to, phenyl, 2-naphthyl, 1-naphthyl, and the like.

The term "halo" as used herein refers to bromo, chloro, fluoro or iodo. Alternatively, the term "halide" as used herein refers to bromide, chloride, fluoride or iodide.

The term "hydroxyl" as used herein refers to the group —OH.

The term "alkoxy" as used herein alone or as part of another group, refers to an alkyl group, as defined herein, appended to the parent molecular moiety through an oxy group. Representative examples of alkoxy include, but are not limited to, methoxy, ethoxy, propoxy, 2-propoxy, butoxy, tert-butoxy, pentyloxy, hexyloxy and the like.

The term "aryloxy" as used herein refers to the group —ArO wherein Ar is aryl or heteroaryl. Examples include, but are not limited to, phenoxy, benzyloxy and 2-naphthyloxy.

The term "amino" as used herein refers to —NH2 in which one or both of the hydrogen atoms may optionally be replaced by alkyl or aryl or one of each, optionally substituted.

The term "alkylthio" as used herein alone or as part of another group, refers to an alkyl group, as defined herein, appended to the parent molecular moiety through a sulfur moiety. Representative examples of alkylthio include, but are not limited to, methylthio, ethylthio, n-propylthio, isopropylthio, n-butylthio, and the like.

The term "carboxy" as used herein refers to the group —CO2H.

The term "quaternary ammonium" as used herein refers to a chemical structure having four bonds to the nitrogen with a positive charge on the nitrogen in the "onium" state, i.e., "$R_4N^+$" or "quaternary nitrogen", wherein R is an organic substituent such as alkyl or aryl. The term "quaternary ammonium salt" as used herein refers to the association of the quaternary ammonium with a cation.

The term "substituted" as used herein refers to replacement of one or more of the hydrogen atoms of the group replaced by substituents known to those skilled in the art and resulting in a stable compound as described below. Examples of suitable replacement groups include, but are not limited to, alkyl, acyl, alkenyl, alkynyl cycloalkyl, aryl, hydroxy, alkoxy, aryloxy, acyl, amino, amido, carboxy, carboxyalkyl, carboxyaryl, halo, oxo, mercapto, sulf[iota]nyl, sulfonyl, sulfonamido, amidino, carbamoyl, dialkoxymethyl, cycloalkyl, heterocycloalkyl, dialkylaminoalkyl, carboxylic acid, carboxamido, haloalkyl, alkylthio, aralkyl, alkylsulfonyl, arylthio, amino, alkylamino, dialkylamino, guanidino, ureido and the like. Substitutions are permissible when such combinations result in compounds stable for the intended purpose. For example, substitutions are permissible when the resultant compound is sufficiently robust to survive isolation to a useful degree of purity from a reaction mixture, and formulation into a therapeutic or diagnostic agent.

The term "solvate" as used herein is intended to refer to a pharmaceutically acceptable solvate form of a specified compound that retains the biological effectiveness of such compound, for example, resulting from a physical association of the compound with one or more solvent molecules. Examples of solvates, without limitation, include compounds of the invention in combination with water, isopropanol, ethanol, methanol, DMSO, ethyl acetate, acetic acid, or ethanolamine.

The term "hydrate" as used herein refers to the compound when the solvent is water.

In another embodiment, an analog of an inhibitor of the chloride transporter according to the invention may have a formula as described in the patent application WO2012/018635. Examples of said analogs include but are not limited to a compound of formula:

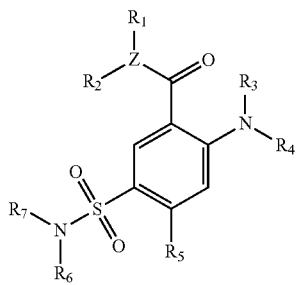

(VI)

or a pharmaceutically acceptable salt thereof, wherein:
  Z is oxygen or nitrogen;
  R1 and R2 are each independently hydrogen, alkyl, aryl, arylalkyl, heteroaryl, heteroaryl alkyl, heterocycloalkyl, or R1 and R2, together with the atom to which they are attached, form a 4-7 membered heterocyclic ring that can have one or more additional heteroatoms and can have one or more substituents, with the proviso that if Z is oxygen, then R2 is not present;
  R3 and R4 are each independently hydrogen, alkyl, cycloalkyl, cycloalkyl alkyl, aryl, arylalkyl, heteroaryl, or heteroarylalky, or R3 and R4, together with the atom' to which they are attached, form a 4-7 membered heterocyclic ring that can have one or more additional heteroatoms and can have one or more substituents;
  R5 is halo, aryl, aryloxy, arylamino, heteroarylamino, heterocycloalkyl, heteroaryl, heteroaryloxy, heterocycloalkoxy, or alkylhio; and
  R6 and R7 are each independently hydrogen, acyl, alkyl, cycloalkyl alkyl, aryl or arylalkyl, or R6 and R7, together with the atom to which they are attached, form a 4-7 membered heterocyclic ring that can have one or more additional heteroatoms and can have one or more substituents.

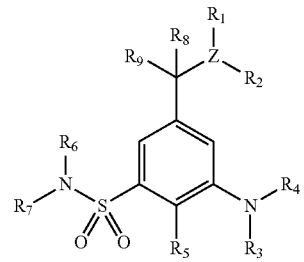

(VII)

or a pharmaceutically acceptable salt thereof, wherein:
  Z is oxygen or nitrogen;
  R1 and R2 are each independently hydrogen, alkyl, aryl, arylalkyl, heteroaryl, heteroarylalkyl, heterocycloalkyl, or R1 and R2, together with the atom to which they are attached, form a 4-7 membered heterocyclic ring that can have one or more additional heteroatoms and can have one or more substituents, with the proviso that if Z is oxygen, then R2 is not present;
  R3 and R4 are each independently hydrogen, alkyl, cycloalkyl, cycloalkyl alkyl, aryl, arylalkyl, heteroaryl, or heteroarylalky, or R3 and R4, together with the atom to which they are attached, form a 4-7 membered heterocyclic ring that can have one or more additional heteroatoms and can have one or more substituents;
  R5 is alkoxy, halo, aryl, aryloxy, alkaryloxy, arylamino, heteroarylamino, heterocycloalkyl, heteroaryl, hetero ryloxy, heterocycloalkoxy, or alkylhio;
  R6 and R7 are each independently hydrogen, acyl, alkyl, cycloalkyl alkyl, aryl or arylalkyl, or R6 and R7, together with the atom to which they are attached, form a 4-7 membered heterocyclic ring that can have one or more additional heteroatoms and can have one or more substituents; and
  R8 and R9 are each independently hydrogen, alkyl, or R8 and R9 together with the atom to which they are attached, form a 3-6 membered substituted or unsubstituted cycloalkyl or heterocycloalkyl ring.

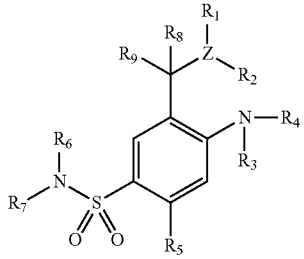

(VIII)

or a pharmaceutically acceptable salt thereof, wherein:
  Z is oxygen or nitrogen;
  R1 and R2 are each independently hydrogen, alkyl, aryl, arylalkyl, heteroaryl, heteroarylalkyl, heterocycloalkyl, or R1 and R2, together with the atom to which they are attached, form a 4-7 membered heterocyclic ring that can have one or more additional heteroatoms and can have one or more substituents, with the proviso that if Z is oxygen, then R2 is not present;

R3 and R4 are each independently hydrogen, alkyl, cycloalkyl, cycloalkyl alkyl, aryl, arylalkyl, heteroaryl, or heteroarylalky, or R3 and R4, together with the atom to which they are attached, form a 4-7 membered heterocyclic ring that can have one or more additional heteroatoms and can have one or more substituents;

R5 is alkoxy, halo, aryl, aryloxy, alkaryloxy, arylamino, heteroarylamino, heterocycloalkyl, heteroaryl, heteroaiyloxy, heterocycloalkoxy, or alkylhio;

R6 nd R7 are each independently hydrogen, acyl, alkyl, cycloalkyl alkyl, aryl or arylalkyl, or R6 and R7, together with the atom to which they are attached, form a 4-7 membered heterocyclic ring that can have one or more additional heteroatoms and can have one or more substituents; and R8 and R9 are each independently hydrogen, alkyl, or R8 and R9 together with the atom to which they are attached, form a 3-6 membered substituted or unsubstituted cycloalkyl or heterocycloalkyl ring.

In another embodiment, an analog of the inhibitor of the chloride transporter may have a formula as described in the patent applications incorporated herein US2007/0155729, GB2207129, in U.S. Pat. Nos. 4,247,550; 3,985,777; 7,282, 519.

In another embodiment, an alternative inhibitor of NKCC activity is selected from the group comprising non-diuretic compounds: protein kinase inhibitors staurosporine and K252a, through SPAK autophosphorylation and substrate phosphorylation of the co-transporter, or the sulfhydryl agents N-ethylmaleimide (NEM) and diamide (Gagnon et al. 2006 Mol. Cell. Biol. 26(2):689-698).

In another embodiment of the invention, the modulator of chloride intracellular level is oxytocin. Oxytocin has been shown to act by reducing intracellular chloride and therefore to act similarly to NKCC1 antagonists.

In another embodiment of the invention, the modulator of chloride intracellular level is not bendroflumethiazide, benzthiazide, buthiazide, chlorothiazide, cyclothiazide, epithiazide, metalthiazide, hydrochlorothiazide, hydro-flumethiazide, methylclothiazide, polythiazide, trichlormethiazide, chlorthalidone, indapamide, metolazone and quinethazone.

Preferably, the modulator of the intracellular chloride level is bumetanide, analogs, functional derivatives and prodrugs thereof.

Another object of the present invention is a modulator of a chloride transporter that improves the outflow of chloride from neurons, preferably through the activation of transporters involved in the outflow of chloride from neurons.

In one embodiment of the invention, the modulator of a chloride transporter improves the outflow of chloride from neurons, preferably through the activation of transporters involved in the outflow of chloride from neurons.

In another embodiment of the invention, said modulator is a modulator of a chloride transporter that improves the outflow of chloride from neurons, preferably through the activation of transporters involved in the outflow of chloride from neurons.

In another embodiment of the invention, said modulator is an activator of a chloride transporter involved in the outflow of chloride from neurons.

In another embodiment of the invention, said modulator is a selective activator of a chloride transporter involved in the outflow of chloride from neurons.

Examples of transporters involved in the outflow of chloride from neurons include, but are not limited to, KCC (wherein KCC stands for "K—Cl co-transporter"), such as, for example, KCC2. In one embodiment, said modulator of a chloride transporter is thus a selective activator of KCC, preferably of KCC2.

Examples of KCC2 activators include but are not limited to: N-ethylmaleimide (NEM), the chloride channel inhibitor 5-nitro-2-(3-phenylpropylamino) benzoic acid (NPPB), CLP257, CLP290 and analogs, functional derivatives and prodrugs thereof.

Examples of KCC2 activators are described in the international patent applications incorporated herein: WO2009/114950; WO2009/097695; WO2010/132999.

In one embodiment of the invention, the modulator improves the expression of a chloride transporter, or improves its presence on the cell surface.

In another embodiment, the selective modulator of KCC improves the expression of a chloride transporter, or improves its presence on the cell surface.

In another embodiment, the activator of KCC improves the expression of a chloride transporter, or improves its presence on the cell surface.

In another embodiment, the selective activator of KCC improves the expression of a chloride transporter, or improves its presence on the cell surface.

In one embodiment of the invention, the modulator of the chloride transporter is involved in the outflow of chloride from neurons.

In another embodiment of the invention, the selective modulator of the chloride transporter is involved in the outflow of chloride from neurons.

In another embodiment of the invention, the activator of the chloride transporter increases the outflow of chloride from neurons.

In another embodiment of the invention, the selective activator of the chloride transporter increases the outflow of chloride from neurons.

In another embodiment, the modulator improves the activity of a chloride transporter, for example is an agonist of a chloride transporter or an antibody or a fragment thereof which activates the chloride transporter.

Examples of such modulators include, but are not limited to, activators of KCC, such as, for example, KCC agonists. In one embodiment, the modulator is an agonist of KCC2.

In one embodiment of the invention, the composition comprises an effective amount of a modulator of intracellular chloride concentration.

In one embodiment of the invention, the effective amount of a modulator of intracellular chloride concentration is calculated in order to reach a desired intracellular concentration of chloride.

Indeed, the Applicant surprisingly showed that the intracellular concentration of chloride is more elevated in VPA rodents than in naïve ones (see Examples).

In one embodiment of the invention, the effective amount of a modulator of intracellular chloride concentration corresponds to the amount to be administered to a subject in need thereof for reaching the intracellular chloride concentration measured in a healthy subject.

In one embodiment of the invention, the effective amount of a modulator ranges from about 0.01 mg to about 500 mg, preferably from about 0.05 mg to about 100 mg, more preferably from about 0.1 mg to about 10 mg and even more preferably from about 0.5 mg to about 1.5 mg.

The present invention also relates to a pharmaceutical composition for treating ASD in a subject in need thereof, wherein said pharmaceutical composition comprises an effective amount of a modulator of intracellular chloride concentration and at least one pharmaceutically acceptable excipient.

As used herein the term "pharmaceutically acceptable excipient" refers to an excipient that does not produce an adverse, allergic or other untoward reaction when administered to an animal, preferably a human. It may include any and all solvents, dispersion media, coatings, antibacterial and antifungal agents, isotonic and absorption delaying agents and the like. For human administration, preparations should meet sterility, pyrogenicity, and general safety and purity standards as required by FDA Office of Biologics standards.

Another object of the invention is a medicament for treating ASD comprising an effective amount of a modulator of intracellular chloride concentration.

The composition, pharmaceutical composition or medicament of the invention may be administered by several routes of administration. Examples of adapted routes of administration include, but are not limited to: subcutaneous, intramuscular, intravenous, intraocular, transdermal, topical, parenteral, intranasal and oral administration, or injection, preferably in utero injection. The type of form for administration will be matched to the severity of the syndrome as well as to the age, weight, sex, etc. . . . of the subject to be treated.

In one embodiment, the composition, pharmaceutical composition or medicament of the invention is in a form adapted for injection, preferably selected from the group comprising solutions, such as, for example, isotonic solution, saline solution, sterile aqueous solutions, dispersions, emulsions, suspensions, solid forms suitable for using to prepare solutions or suspensions upon the addition of a liquid prior to use, such as, for example, powder, freeze-dried compositions, liposomal forms and the like.

In one embodiment, the composition, pharmaceutical composition or medicament of the invention is in a form adapted to oral administration. In one embodiment, the form adapted to oral administration is a solid form selected from the group comprising tablets, pills, capsules, soft gelatin capsules, sugarcoated pills, orodispersing tablets, effervescent tablets or other solids. In another embodiment, the form adapted to oral administration is a liquid form, such as, for example, a drinkable solution, a buccal spray, liposomal forms and the like.

In one embodiment, the composition, pharmaceutical composition or medicament of the invention is in a form adapted for local delivery via the nasal and respiratory routes. Examples of formulations suitable for nasal administration include but are not limited to, nasal solutions, sprays, aerosols and inhalants.

In one embodiment, the composition, pharmaceutical composition or medicament of the invention is in a form adapted to topical administration. Examples of formulations adapted to topical administration include, but are not limited to, ointment, paste, eye drops, cream, patch, such as, for example, transdermal patch, gel, liposomal forms and the like.

In one embodiment, the composition, pharmaceutical composition or medicament of the invention is in the form of, or comprises, liposomes and/or nanoparticles.

In one embodiment, the composition, pharmaceutical composition or medicament of the invention further comprises some excipients, such as, for example, surfactants (e.g. hydroxypropylcellulose); suitable carriers, such as, for example, solvents and dispersion media containing, for example, water, monosodium or disodium phosphate, sodium, potassium, calcium or magnesium chloride, ethanol, polyol (e.g. glycerol, propylene glycol, and liquid polyethylene glycol, and the like), suitable mixtures thereof, and vegetable oils, such as, for example, peanut oil and sesame oil; isotonic agents, such as, for example, sugars or sodium chloride; coating agents, such as, for example, lecithin; agents delaying absorption, such as, for example, aluminum monostearate and gelatin; preservatives, such as, for example, benzalkonium chloride, benzethonium chloride, chlorobutanol, thimerosal and the like; buffers, such as, for example, boric acid, sodium and potassium bicarbonate, sodium and potassium borates, sodium and potassium carbonate, sodium acetate, sodium biphosphate and the like; tonicity agents, such as, for example, dextran 40, dextran 70, dextrose, glycerin, potassium chloride, propylene glycol, sodium chloride; antioxidants and stabilizers, such as, for example, sodium bisulfite, sodium metabisulfite, sodium thiosulfite, thiourea and the like; nonionic wetting or clarifying agents, such as, for example, polysorbate 80, polysorbate 20, poloxamer 282 and tyloxapol; viscosity modifying agents, such as, for example dextran 40, dextran 70, gelatin, glycerin, hydroxyethylcellulose, hydroxmethylpropylcellulose, lanolin, methylcellulose, petrolatum, polyethylene glycol, polyvinyl alcohol, polyvinylpyrrolidone, carboxymethylcellulose; and the like.

In one embodiment of the invention, the composition, pharmaceutical composition or medicament of the invention may be used in conjunction with delivery systems that facilitate delivery of the agents to the subject. The drug delivery is directly administered to the human fetus or human embryo rather than to the pregnant woman, via a uterine target such as for example, the supporting vasculature, the placenta, or the vessels of the umbilical cord.

For example, various placenta permeability enhancers may be used to transiently and reversibly increase the permeability of the placenta.

In one embodiment of the invention, the composition, pharmaceutical composition or medicament of the invention may be used in conjunction with delivery systems that facilitate delivery of the agents to the central nervous system. For example, various blood brain bather (BBB) permeability enhancers may be used to transiently and reversibly increase the permeability of the blood brain barrier to a treatment agent. Such BBB permeability enhancers include but are not limited to leukotrienes, bradykinin agonists, histamine, tight junction disruptors (e.g., zonulin, zot), hyperosmotic solutions (e.g., mannitol), cytoskeletal contracting agents, and short chain alkylglycerols (e.g., 1-O-pentylglycerol). Oral, sublingual, parenteral, implantation, nasal and inhalational routes can provide delivery of the active agent to the central nervous system. In some embodiments, the compounds of the present invention may be administered to the central nervous system with minimal effects on the peripheral nervous system.

The blood-brain barrier (BBB) is a physical barrier and system of cellular transport mechanisms between the blood vessels in the central nervous system (CNS) and most areas of the CNS itself. The BBB maintains homeostasis by restricting the entry of potentially harmful chemicals from the blood, and by allowing the entry of essential nutrients. However, the BBB can pose a formidable bather to delivery of pharmacological agents to the CNS for treatment of disorders or maintaining or enhancing normal and desirable brain functions, such as cognition, learning, and memory.

The present invention can also relate to a prodrug of the modulator of the intracellular chloride concentration within neurons or an encapsulation of said modulator.

In one embodiment, the composition, pharmaceutical composition or medicament of the invention is a prodrug of the selective modulator of intracellular chloride concentration within neurons.

In another embodiment, the composition, pharmaceutical composition or medicament of the invention is a prodrug of the inhibitor of chloride importation within neurons.

In another embodiment, the composition, pharmaceutical composition or medicament of the invention is a prodrug of the selective inhibitor of chloride importation within neurons.

In another embodiment, the composition, pharmaceutical composition or medicament of the invention is a prodrug of the activator of chloride outflow from neurons.

In another embodiment, the composition, pharmaceutical composition or medicament of the invention is a prodrug of the selective activator of chloride outflow from neurons.

Prodrugs as described herein are capable of passage across the blood-brain barrier and may undergo hydrolysis by CNS esterases to provide the active compound.

Prodrugs as described herein are capable of passage across the placenta.

Prodrugs provided herein may also exhibit improved bioavailability, improved aqueous solubility, improved passive intestinal absorption, improved transporter-mediated intestinal absorption, protection against accelerated metabolism, tissue-selective delivery, less (or fewer) side effects, lessened or no deleterious drug interaction with other medications, and/or passive enrichment in the target tissue.

The term "prodrug" as used herein refers to a compound that is converted under physiological conditions, by solvolysis or metabolically to a specified compound that is pharmaceutically/pharmacologically active. The "prodrug" can be a compound of the present invention that has been chemically derivatized such that it retains some, all or none of the bioactivity of its parent drug compound and is metabolized in a subject to yield the parent drug compound. The prodrug of the present invention may also be a "partial prodrug" in that the compound has been chemically derivatized such that it retains some, all or none of the bioactivity of its parent drug compound and is metabolized in a subject to yield a biologically active derivative of the compound.

Prodrugs can be formed by attachment of biocompatible polymers, such as those previously described including polyethylene glycol (PEG), to compounds of the present invention using linkages degradable under physiological conditions. See also Schacht, et al. (1997) Poly(ethylene glycol) Chemistry and Biological Applications, American Chemical Society, San Francisco, Calif. 297-315. Attachment of PEG to proteins can be employed to reduce immunogenicity and/or extend the half-life of the compounds provided herein. Any conventional PEGylation method can be employed, provided that the PEGylated agent retains at least some pharmaceutical activity.

In one embodiment, the selective inhibitor of the invention is bumetanide-PEGylated.

In one embodiment, the present invention further provides prodrugs comprising the compounds described herein. The prodrugs can be formed utilizing a hydrolyzable coupling to the compounds described herein. Ettmayer, et al. (2004) J. Med. Chem. 47(10): 2394-2404; Testa and Mayer (2003) Hydrolysis in Drug and Prodrug Metabolism: Chemistry, Biochemistry and Enzymology Wiley-Verlag Helvetica Chimica Acta, Zuerich (Chapters 1-1): 1-780.

In another embodiment, the composition, the pharmaceutical composition or the medicament of the invention is administered to the pregnant woman.

In another embodiment, the composition, the pharmaceutical composition or the medicament of the invention is administered to the pregnant woman at gestational age 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41.

In another embodiment, the composition, the pharmaceutical composition or the medicament of the invention is administered at the preterm stage to the pregnant woman.

In another embodiment, the composition, the pharmaceutical composition or the medicament of the invention is administered at the early term stage to the pregnant woman.

In another embodiment, the composition, the pharmaceutical composition or the medicament of the invention is administered at the full term stage to the pregnant woman.

In another embodiment, the composition, the pharmaceutical composition or the medicament of the invention is administered at the late term stage to the pregnant woman.

In another embodiment, the composition, the pharmaceutical composition or the medicament of the invention is administered at the postmature stage to the pregnant woman.

In another embodiment, the composition, the pharmaceutical composition or the medicament of the invention is administered to the pregnant woman before delivery, in particular, at least once 24 h, 20 h, 18 h, 12 h, 8 h, 6 h, 4 h, 2 h before delivery.

In one embodiment of the invention, the composition, the pharmaceutical composition or the medicament of the invention is administered at least once a day, preferably twice a day, more preferably at least three times a day.

In one embodiment of the invention, the daily amount of a modulator to be administered to a subject ranges from about 0.01 mg/day to about 500 mg/day, preferably from about 0.05/day mg to about 100 mg/day, more preferably from about 0.1 mg/day to about 10 mg/day and even more preferably from about 0.5 mg/day to about 1.5 mg/day.

In another embodiment of the invention, the administration dose of the pharmaceutical composition is determined by the skilled artisan and personally adapted to each subject.

In one embodiment of the invention, the modulator is administered in a sustained-release form. In one embodiment of the invention, the composition comprises a delivery system that controls the release of the modulator. Examples of suitable carriers for sustained or delayed release include, but are not limited to, gelatin; gum Arabic; xanthane polymers; thermoplastic resins such as, for example polyvinyl halides, polyvinyl esters, polyvinylidene halides and halogenated polyolefins; elastomers such as, for example, brasiliensis, polydienes, and halogenated natural and synthetic rubbers; and flexible thermoset resins such as polyurethanes, epoxy resins; biodegradable polymers and the like.

In another embodiment of the invention, the modulator of the present invention is administered in combination with other therapies that could include: speech therapy, behavioral therapy, sensory integration occupational therapy, special education, or individualized educational plans, and, when necessary, treatment of physical abnormalities.

In one embodiment of the invention, the composition of the invention is for treating behavioral and/or cognitive symptoms associated with ASD. In one embodiment, the administration to a subject in need thereof of the composition of the invention results in the alleviation of behavioral symptoms of ASD.

Examples of behavioral and/or cognitive symptoms of ASD include, but are not limited to, hyperactivity, stereotypy, anxiety, seizure, impaired social behavior, cognitive delay, hypersensitivity to sensory stimuli, mood disorders, disrupt sleep patterns, irritability, aggression or self-injurious behavior, mental retardation, learning disabilities (such as, for example, delays in learning how to sit, walk and talk), nervous or cluttered speech, difficulty with face encoding and deficient central executive, working, phonological and/or visual-spatial memories.

In one embodiment of the invention, the behavioral and/or cognitive symptom associated with ASD is not Fragile X syndrome.

Methods for assessing the efficacy of the treatment are readily measurable by routing procedures familiar to a physician, such as, for example, use of scales. Examples of scales that may be used for assessing the efficacy of the treatment of ASD include, but are not limited to, the ABC scale, the GRAM scale and the CGI scale.

According to one embodiment of the invention, the composition of the invention is for alleviating the occurrence of ocular symptoms and/or othorhinolaryngo local manifestations associated with ASD. In one embodiment, the administration to a subject in need thereof of the composition of the invention results in the alleviation of ocular symptoms and othorhinolaryngo local manifestations and/or in the reduction of the occurrence of said symptoms, such as, for example, in the reduction of the occurrence of ophthalmologic problems including strabismus, otitis media and sinusitis.

According to one embodiment of the invention, the composition of the invention is for treating synaptic defects/symptoms associated with ASD. In one embodiment, the administration to a subject in need thereof of the composition of the invention results in the alleviation of synaptic defects associated with ASD.

Examples of synaptic defects/symptoms associated with ASD include, but are not limited to, defective synaptic morphology (such as, for example, an abnormal number, length, and/or width of dendritic spines) and defective synaptic function (such as, for example, enhanced long-term depression (LTD) and/or reduced long-term potentiation (LTP)).

The Applicant surprisingly showed that delivery was a key event in the development of ASD (see Examples). Therefore, in one embodiment, the composition of the invention is administered to a pregnant woman. According to the invention, the term "pregnant woman" refers to a woman from the conception date to the end of the delivery.

In one embodiment of the invention, the composition is perinatally administered to a child. As used herein, the term "perinatally" refers to a few hours after birth, preferably 10, 8, 6, 5, 4, 3, 2 or 1 hour(s) after birth. Preferably, this embodiment applies following delivery complications of the child.

In another embodiment, the composition of the invention is perinatally administered when the subject presents a risk of developing ASD.

In another embodiment, the composition of the invention is perinatally administered when the subject suffered from delivery complications.

In another embodiment, the composition of the invention is perinatally administered when the subject suffered from anoxia during delivery.

In one embodiment, the composition is administered perinatally when the subject presents a familial history of ASD.

In one embodiment, the composition is administered to a pregnant woman when the subject of the invention has been prenatally diagnosed with ASD, preferably when the subject presents genetic mutations, epigenetic modifications, phenotypic variations or chromosomal abnormalities associated with ASD.

Examples of genetic mutations, epigenetic modifications, phenotypic variations or chromosomal abnormalities associated to ASD include but are not limited to: contactin (CNTN), contactin-associated gene (CNTNAP) for example structural variations in CNTNAP2, neuroligin (NLGN), SHANK, Engrailed 2 (EN2) gene, serotonin-transporter-linked polymorphic region (5HTTLPR), mTOR/PI3kinase pathway, calcium channel (CACNA1C), NRXN1, 22q11.2 and 22q13 deletions, deletions in CNTNAP5 and DOCK 4, deletions and duplications at 16 µl, duplications at 15q11-13, deletions in the 15q11.2-q14, rare recurrent deletions or duplications at 1q21, 1p, 1p21.3, 1 g25.1-q25.2, 2p16.3, 2q37, 3p26.3, 5q14.3, 6p23.1, 7q11.23, 7q35-q36.1, 7q36.2, 8p23.3, 9p33.1, 11q13, 10q, 13q13.2, 15q11-13, 16p11.2, 16p13.2, 17p, 20p, 22q11, 22q13.

In one embodiment, the composition is administered to a pregnant woman or to the subject of the invention when the subject presents a familial history of ASD. In particular, a said pregnant woman has already one child with neural tube defect.

In another embodiment, the composition is administered to a pregnant woman or to the subject of the invention when the subject presents a risk of developing ASD due to complications or expositions to diverse factors during pregnancy.

In one embodiment, the pregnant woman presented hypertension.

In one embodiment, said subject was exposed in utero to an infection before delivery. Examples of such infections include but are not limited to: congenital rubella syndrome or cytomegalovirus.

Increased risk factors of ASD could be due to pregnant women's diet. Examples of such risk factors include but are not limited to: diabetes, deficiencies in key nutrients in said pregnant women's diet, such as Zinc, Selenium, vitamin B 12, vitamin 6, vitamin D, Omega 3 and Folate.

In another embodiment, said subject was exposed in utero to environmental or toxic agents that increase risks of ASD.

Increased risk factors of ASD could be due to the exposition of the subject of the invention to environmental factors that include heavy metal, antibiotics, food preservatives, toxic additives and environmental toxins.

Examples of such toxic agents include but are not limited to: teratogens agents, misoprostol, ethanol (grain alcohol), flavonoids in food, tobacco smoke, herbicides.

Subject

In one embodiment of the invention, the subject is a male. In another embodiment of the invention, the subject is a female.

In one embodiment, the subject of the invention is a human embryo.

In another embodiment, the subject of the invention is a human fetus.

In another embodiment, the subject of the invention is a new born child.

In one embodiment of the invention, the subject is a young child. As used herein, the term "young child" refers to a child from 0; 1; 2; 3; 4; 5; 6; 7; 8; 9; 10; 11 months old; 1 year old; 1 year and 3 months old; 1 year and 6 months old; 1 year and 9 months old; 2 years; 2 years and 3 months old; 2 years and 6 months old; 2 years and 9 months old; 3 years old.

In one embodiment, the subject of the invention is a healthy subject.

In another embodiment, the subject of the invention has risk of developing an ASD.

In another embodiment, the subject of the invention has a predisposition of developing ASD.

In one embodiment, the subject of the invention suffered from complications during delivery.

In another embodiment, the subject of the invention suffered from anoxia during delivery.

In another embodiment, the subject of the invention has been diagnosed as having an ASD.

In one embodiment, said subject presents a familial history of ASD.

In one embodiment of the invention, the detection of the mutations associated to ASD is performed on a sample from the subject, preferably a body fluid sample from the subject. Examples of body fluids include, but are not limited to, blood, plasma, serum, saliva, lymph, ascetic fluid, cystic fluid, urine, bile, nipple exudate, synovial fluid, bronchoalveolar lavage fluid, sputum, amniotic fluid, chorionic villi, peritoneal fluid, cerebrospinal fluid, pleural fluid, pericardial fluid, semen, saliva, sweat and alveolar macrophages. Preferably, said body fluid is plasma or serum.

In one embodiment of the invention, the method of the invention comprises subcutaneously, intramuscularly, intravenously, intraocularly, transdermally, topically, parenterally, intranasally or orally administering the modulator of the invention, or its injection preferably in utero injection.

In one embodiment of the invention, the method of the invention comprises administering the modulator of the invention only once.

In another embodiment of the invention, a daily amount of a modulator ranging from about 0.01 mg/day to about 500 mg/day, preferably from about 0.05/day mg to about 100 mg/day, more preferably from about 0.1 mg/day to about 10 mg/day and even more preferably from about 0.5 mg/day to about 1.5 mg/day is administered to the subject.

Method of Treatment

The present invention also relates to a method for decreasing the intracellular concentration of chloride in a subject in need thereof, preferably the neuronal intracellular concentration of chloride.

Another object of the invention is a method for modulating the intracellular chloride concentration of a subject in need thereof, wherein the method comprises administering to the subject in need thereof an effective amount of a modulator of a chloride transporter.

The present invention also relates to a method for decreasing the driving force of GABA in a subject in need thereof.

In one embodiment of the invention, the method comprises administering to the subject an effective amount of a modulator of a chloride transporter.

In one embodiment of the invention, said effective amount is calculated in order to reach a desired intracellular concentration of chloride.

In one embodiment of the invention, the method comprises administering to the subject in need thereof the composition, the pharmaceutical composition or the medicament of the invention.

EXAMPLES

Figure 1:
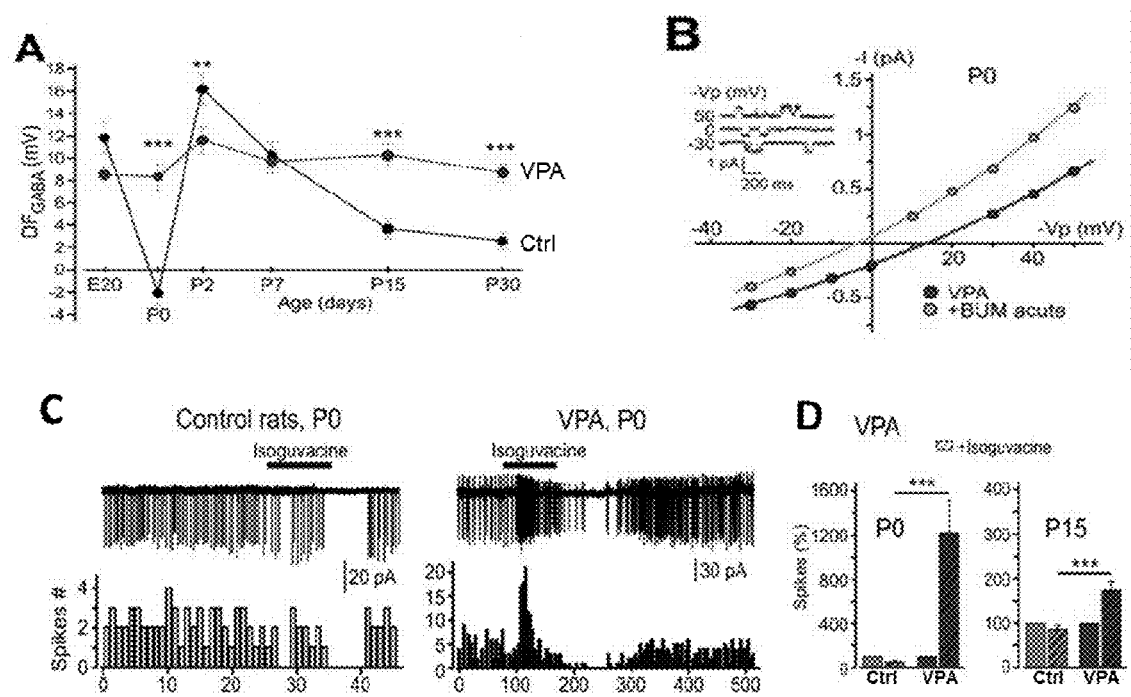
FIG. 1 represents histograms on the driving force for $GABA_AR$ in control (ctrl) and VPA rats. (A) shows age—dependence of $GABA_AR$ driving force ($DF_{GABA}$) in control and VPA rats at E20, P0, P2, P7, P15 and P30. Values are significantly different at all ages studied except at P7 (at P0, P15 and P30*$P<0.005$; at P2$P<0.05$). (B) shows Intensity-Voltage relationships of $GABA_AR$ single channel currents at P0 in artificial cerebrospinal fluid (ACSF) and bumetanide (10 µM) in VPA rats. Inset-single channels openings at different holding potentials. (C) shows excitatory action of the GABAAR agonist isoguvacine (10 µM) on spontaneous spiking recorded in cell-attached configuration in VPA rats. Time-course of spike frequency changes is shown under each trace. (D) shows average values of normalized to control spike frequency for rats. P0: control rats (n=9), VPA rats (n=5), *$P<3.1\times10^{-4}$; P15: control rats (n=11), VPA rats (n=13), *$P<3.5\times10^4$.

The present invention is further illustrated by the following examples.

Materials and Methods
Valproate Rat Model of Autism

Time-mated female Wistar rats at gestational day E7-8 were housed under standard laboratory conditions. The in utero valproic acid (VPA) rodent model of autism spectrum disorders has been previously described in detail. Briefly, the sodium salt of VPA (Sigma-Aldrich) was dissolved in physiological saline solution to a concentration of 300 mg/ml. Pregnant rats received a single intra-peritoneal dose of 600 mg/kg on gestational day 12 (E12). The control dams received a single similar volume injection of saline at the same gestational time-point. Dams were housed individually and allowed to raise their own litters. The offspring were used for experiments on embryonic day 20 (E20) and postnatal (P) days 0, 2, 4, 7, 15 and 30 (after being weaned at P23). Experiments were carried out on offspring of either sex.

Slice Preparation

Experiments were performed on fetuses and neonatal rat pups. We removed E20 rats from deeply anesthetized dams [subcutaneous injection of a mixture of xylazine (Rompun 2%; used at 0.05%) and ketamine (Imalgene 1000 used at 50 g/l)]. Hippocampal slices (300-500 nm thick) were prepared using a Microm tissue slicer (International GmbH, Germany) as described previously (Tyzio et al. 2006 Science 314, 1788; Tyzio et al, 2008, Eur J. Neurosci. 27(10):2515-28). Slices were kept in oxygenated (95% $O_2$/5% $CO_2$) artificial cerebrospinal fluid (ACSF) of the following composition (in mM): NaCl 126, KCl 3.5, $CaCl_2$ 2.0, $MgCl_2$ 1.3, $NaHCO_3$ 25, $NaH_2PO4$ 1.2 and glucose 11 (pH 7.4) at room temperature (20-22° C.) at least 1 hour before use.

Electrophysiology

For recordings, slices were placed into a conventional fully submerged chamber superfused with ACSF at a rate of 2-3 ml/min at room temperature. Patch clamp recordings from visually identified CA3 pyramidal cells in cell-attached configuration were performed using EPC-10 amplifier (HEKA Elektronik Dr. Schulze GmbH, Lambrecht/Pfalz, Germany). Patch pipette solution for recordings of single $GABA_A$ channels contained (in mM): NaCl 120, KCl 5, TEA-Cl 20, 4-aminopyridine 5, $CaCl_2$ 0.1, $MgCl_2$ 10, glucose 10, Hepes-NaOH 10 buffered to pH 7.2-7.3 and GABA 2 μM. Analysis of currents through single channels and current-voltage relationships were performed using Clampfit 9.2 (Axon Instruments, Union City, Calif.). Recordings were digitized (10 kHz) online with Digidata-1200 interface card (Axon Instruments, Union City, Calif.) and analyzed offline with Axon package, MiniAnalysis (S (Synaptsoft, Decatur, Ga.), and Origin (Microcal Software, Northampton, Mass.).

Whole-Cell Recordings

Standard whole-cell recordings were performed in coronal neocortical rat or mouse brain slices at room temperature (20-22° C.) from the soma of hippocampal CA3 neurons using an EPC-10 (HEKA Elektronik, Germany) amplifier and filtered at 3-10 kHz. The internal solution contained (in mM): 130 K-gluconate, 10 Na-gluconate, 4 NaCl, 4 MgATP, 4 phosphocreatine, 10 HEPES, and 0.3 GTP (pH 7.3 with KOH). Biocytin (final concentration 0.3-0.5%) was added to the pipette solution to label the neurons from which recordings were obtained. Neurons were visualized by using infrared DIC video microscopy. Spontaneous postsynaptic currents were recorded for 15 mM at the reversal potentials for GABAergic currents (−70 mV). It should be specifically noted that all recordings were made in normal ACSF (1.3 mM $MgCl_2$). Stored data were analyzed using the Mini Analysis 6.0.3 (Synaptosoft Inc., Chapell Hill, N.C.) and Origin (MicroCal, Northampton, Mass.) software. To minimize potential sampling bias, the pups from at least three deliveries for each condition were studied. Data are expressed as mean±S.E.M.

Extracellular field potentials and multi-unit activity (MUA) recordings Recording were made in the hippocampal slices using tungsten wire electrodes (diameter: 50 μm, California Fine Wire, Grover Beach, Calif.) and a low-noise multichannel DAM-8A amplifiers (WPI, GB; low-pass filter: 0.1 Hz; high-pass filter: 3 KHz; gain: ×1000). The signals were digitized using an analogue-to-digital converter (Digidata 1440A, Axon Instruments, USA). pCLAMP 10.1, Clampfit 10.1 (Axon Instruments, USA), MiniAnalysis 6.03 (Synaptosoft, Decatur, Calif.) and Origin 7.5 (Microcal Software, USA) programs were used for the acquisition and analysis of the synaptic activities. Sampling interval per signal was 100 microseconds (10 kHz).

In Vivo Recordings of EEG

Head-fixed rat pups of age P13-P15 were prepared for extracellular recording under isoflurane anesthesia. The skin and periosteum were removed from the skull, which was then covered by glue and dental cement except for a 4-9 $mm^2$ window above the somatosensory cortex from one or two hemispheres for the silicon probe penetration (4.0-4.2 mm lateral to midline and 2.2-2.5 mm caudal to bregma) and for the reference electrode (1.0-1.5 mm lateral to midline and 6.0-6.5 mm caudal to bregma). The rat was positioned in the stereotaxic apparatus. A 1 mm-diameter burr hole was drilled in the skull; the dura was cut and removed. Recordings were made 1 h after recovery from anesthesia. Pups were kept restrained for <3 h and were closely monitored for signs of stress and to ensure that they spent a normal proportion of their time sleeping. The outside temperature was maintained between 35 and 36° C. The animals were kept in low-light conditions throughout all experiments. 16-site linear silicone probe (NeuroNexus Technologies) coupled to a direct-current amplifier (Molecular Devices) and dunked previously in fluorescent dye (DiI, Invitrogen) was slowly penetrated via the hole at 3200 nm depth under the angle 30° in the coronal plane. EEGs were recorded during 2 hours, using a 16-channel amplifier (A-M System, Inc.) and digitized at 5 kHz using Axoscope software (Molecular Deviced). Recordings were amplified and high-pass filtered at 0.3 Hz in Axoscope. Silicone probe location was verified postmortem via dye localization. To quantify the frequency band integral power the traces were band-pass filtered at frequency bands 6540.5-4 Hz) θ-(4-7 Hz), α-(7-12 Hz), β-(12-25 Hz), Low γ-(25-60 Hz), High γ-(60-120 Hz) and Fast oscillations-(120-500 Hz)). Fast Fourier Transform (FFT) was applied with Clampfit (Molecular Devices). Integrals of FFT power spectra were taken and averaged with OriginPro (OriginLab Corporation).

Vocalization

To induce ultrasonic vocalizations, mouse pups were isolated individually from their mother on postnatal day 8, and were placed into an isolation box (23×28×18 cm) located inside a sound attenuating isolation cubicle (54×57× 41 cm; Coulbourn Instruments, Allentown, Pa., USA), and evaluated for ultrasonic vocalizations during a three minutes test. An ultrasound microphone (Avisoft UltraSoundGate Condenser microphone capsule CM16/CMPA, Avisoft Bioacoustics, Berlin, Germany), placed in the roof of the box, was sensitive to frequencies of 10 to 250 kHz. Vocalizations were recorded using the Avisoft Recorder software (version 4.2) with a sampling rate of 250 kHz in 16 bit format. For acoustical analysis, recordings were transferred to SASLab Pro (version 5.2; Avisoft Bioacoustics) and a fast Fourier transformation was conducted (512 FFT-length, 100% frame, Hamming window and 75% time window overlap). The accuracy of call detection was verified manually by an educated user. A Pearson correlation coefficient was computed to assess the relationship between Automatic and Manual analysis. There was 0.99 correlation between the two variables.

Statistics

The data from electrophysiological study were analyzed with two tailed t-test and one-way ANOVA Fisher's LSD post-hoc test. For quantification of western blots we used unpaired t-tests between control and VPA. For behavior, experimenters were blind to the treatment or genotype during testing and analyzing. All data are presented as mean±S.E.M. (error bars).

Pharmacology

Bumetanide (10 µM), Oxytocin (1 µM) and Isoguvacine (2 µM) were directly added to the perfusion solutions. Bumetanide pretreatment (2-2.5 mg/kg) was given to the dams in drinking water. All drugs used were purchased from Sigma. SSR126768A (Sanofi-Synthelabo) pretreatment (1 mg/kg) was given to the dams in drinking water.

RESULTS

Example 1

Developmental Excitatory/Inhibitory GABA Sequence is Abolished in Hippocampal CA3 Pyramidal Neurons in VPA Rats The driving force for $GABA_AR$ ($DF_{GABA}$) used as an index of $[Cl^-]_i$ was elevated in fetal hippocampal CA3 pyramidal neurons (E20-21) in naive rats and reduced to adult values at P15-30 with an abrupt reduction restricted to the delivery period (FIG. 1A; table 1). In contrast, $DF_{GABA}$ was elevated in fetal, early postnatal stages and P15-30 in VPA rats (FIG. 1A; table 1). Acute applications of the specific NKCC1 chloride importer antagonist bumetanide (10 µM) significantly decreased $[Cl^-]_i$ and $DF_{GABA}$ at P0 in VPA neurons (FIG. 1B; table 2). Therefore, GABA depolarizes VPA in a bumetanide-sensitive manner.

TABLE 1

Developmental changes of the driving force for $GABA_ARs$ ($DF_{GABA}$) in hippocampal CA3 pyramidal cells in 2 models of autism.
$DF_{GABA}$ (mV), mean ± S.E.

| | Control rats | VPA | Statistics |
|---|---|---|---|
| E20 | 11.8 ± 1.4 (n = 8) | 8.5 ± 0.6 (n = 9) | Control vs. VPA n.s. |
| P0 | −2.1 ± 0.8 (n = 22) | 8.2 ± 1.3 (n = 29) | Control vs. VPA P < 0.001 |
| P2 | 16.2 ± 1.1 (n = 35) | 11.7 ± 1.4 (n = 24) | Control vs. VPA P < 0.01 |
| P7 | 10.2 ± 1.2 (n = 29) | 9.7 ± 1.1 (n = 26) | Control vs. VPA n.s. |
| P15 | 3.6 ± 0.7 (n = 21) | 10.2 ± 1 (n = 25 | Control vs. VPA P < 0.001 |
| P30 | 2.5 ± 0.8 (n = 19) | 8.7 ± 0.8 (n = 25) | Control vs. VPA P < 0.001 |

Control rats and VPA rats (numbers correspond to FIG. 1A).

TABLE 2

Acute application of bumetanide (10 µM) shifts $DF_{GABA}$ in P0 hippocampal CA3 pyramidal cells from depolarizing to hyperpolarizing.

| | $DF_{GABA}$ mV), mean± | Statistics |
|---|---|---|
| Control rats | −2.1 ± 0.8 (n = 22) | |
| Control + BUM acute | −5.3 ± 0.7 (n = 17) | Control vs. Control + BUM acute P < 0.01 |
| VPA rats | 8.2 ± 1.3 (n = 29) | |
| VPA + BUM acute | −2.4 ± 1.2 (n = 21) | VPA vs. VPA + BUM acute P < 0.001 |

The statistics presented by ANOVA test followed by post hoc Fisher test.

Example 2

Maternal Pretreatment with Bumetanide in VPA Rats In Vitro

Figure 2:
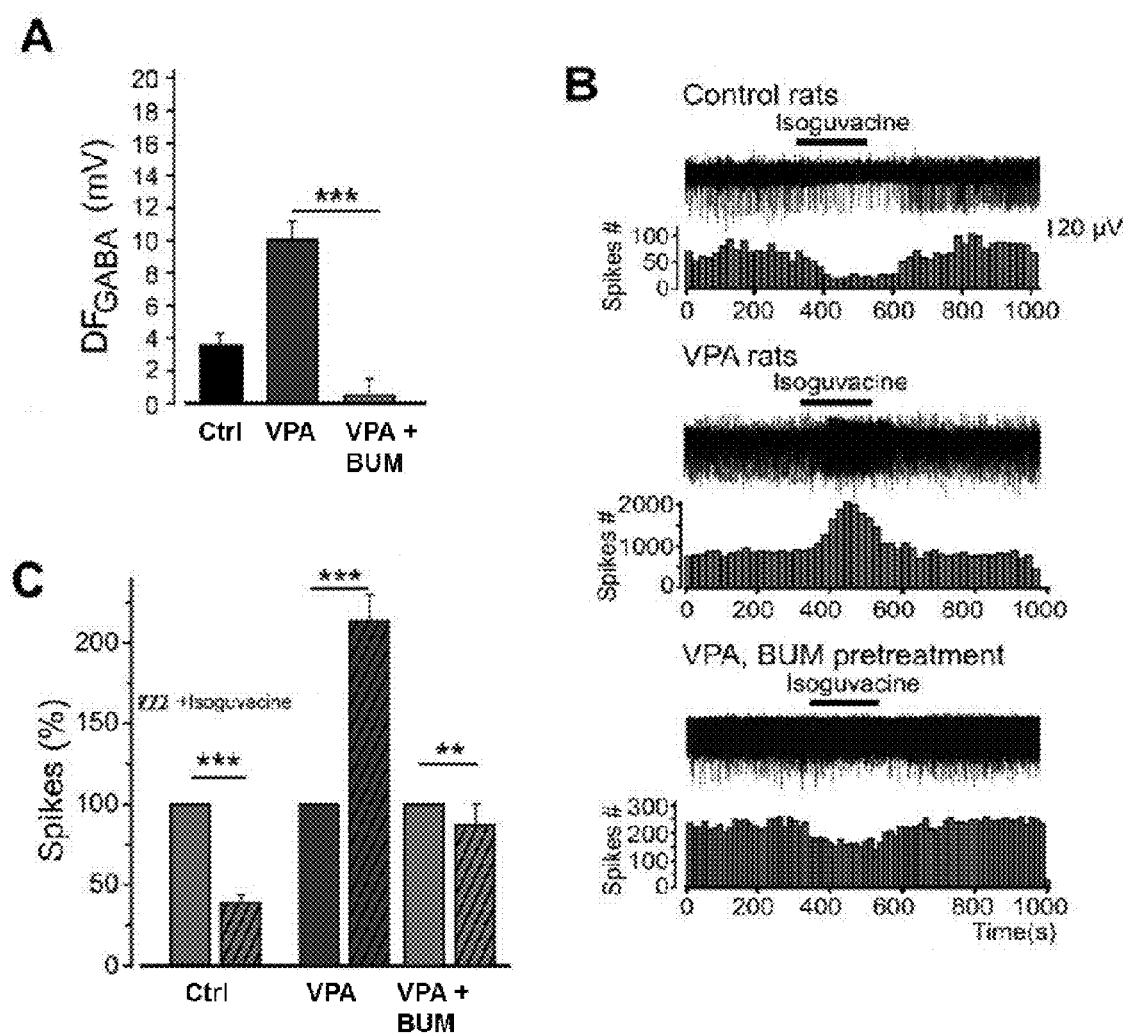
FIG. 2 represents histograms on the effect of maternal pretreatment with Bumetanide in vitro. (A) shows average values of $DF_{GABA}$ measured in hippocampal CA3 pyramidal neurons at P15 in control (3.4±0.6 mV, n=22), VPA (10.2±1.0 mV, n=25) and in VPA rats pretreated with bumetanide (0.4±1.1 mV, n=58, *$P<0.001$). Note that pretreatment with bumetanide shifts $DF_{GABA}$ from depolarizing to almost isoelectric level. (B) shows effects of isoguvacine (10 µM) in rats: Representative traces of spontaneous extracellular field potentials recorded in hippocampal slices at P15 in control, VPA and VPA rats pretreated with bumetanide. Corresponding time-courses of spike frequency changes are shown under each trace. (C) shows average histograms of normalized spike frequency in rats. Isoguvacine decreased the spikes frequency in control rats (to 38.9±5.1%, n=3, *$P<0.001$), increased it in VPA rats (to 213.5±16.3%, n=6, *$P<0.001$) and decreased it in VPA rats pretreated with bumetanide (to 82.8±10.7%, n=9, $P<0.05$).

To test whether the depolarizing actions of GABA were associated with neuronal excitation, in naive neurons, the specific $GABA_AR$ agonist isoguvacine (2 µM) inhibited or did not affected spike frequency in cell-attached recordings at P0 (FIG. 1C-D), and in field potential recordings at P15 (FIG. 2B; table 3). In contrast, isoguvacine increased spike frequency in VPA neurons in cell-attached recordings at P0 (FIG. 1C-D) and P15 (FIG. 1D) and in field potential recordings at P15 (FIG. 2B, C). Therefore, GABA excites newborn and juvenile VPA neurons.

TABLE 3

Maternal pretreatment with bumetanide shifted the effects of isoguvacine from excitation to inhibition in offsprings (P15) in VPA.

| | Effects of isoguvacine on frequency of spikes in extracellular recordings (% of control), mean ± S.E. |
|---|---|
| Control rats | 38.9 ± 5.1 (n = 3), P < 0.001 |
| VPA rats | 213.5 ± 16.3 (n = 6), P < 0.001 |
| BUM pretreatment | 82.8 ± 10.7 (n = 9), P < 0.05 |

The statistics are presented by two sample two tail t test.

Figure 3:
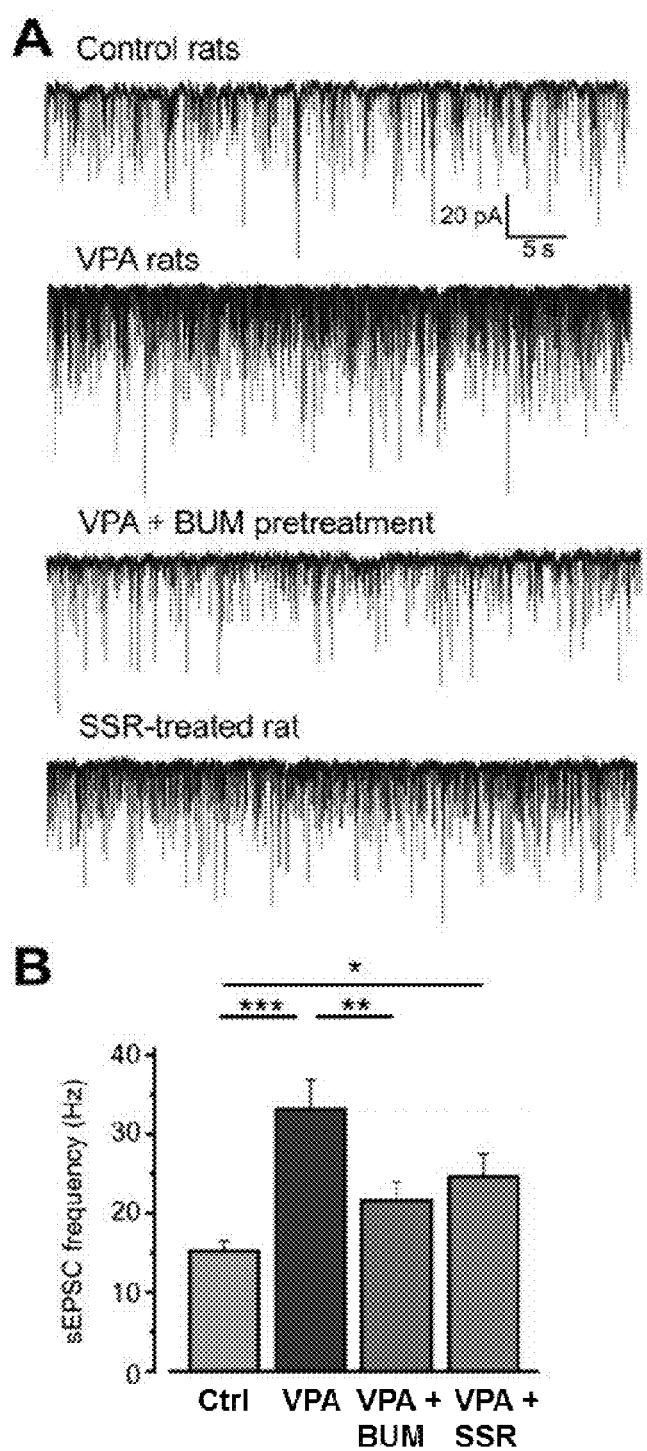
FIG. 3 represents whole-cell voltage clamp recordings of spontaneous excitatory postsynaptic currents (sEPSCs) at −70 mV from individual hippocampal CA3 pyramidal neurons in acute brain slices from P15 VPA rats and respective control and bumetanide or SSR pretreated animals. (A) shows representative traces of sEPSCs recorded from rats. Note that maternal pretreatment of animals with bumetanide decreases sEPSCs frequency, whereas treatment with SSR increases spontaneous activity of neuronal networks in rats. (B) shows a verage values±S.E.M of sEPSCs frequencies. Control rats (n=8) and VPA rats (n=21, *$P<6.2\times10^{-4}$), and VPA rats with maternal pretreatment with bumetanide (n=21, $P<0.003$) and SSR-treated rats (n=32, ***$P<8.0\times10^{-5}$). One-way ANOVA Fisher's LSD post-hoc test. Data presented as means±S.E.M.

If the polarity of GABA actions at delivery produces long terms effects in offsprings, then restoring low $[Cl^-]_i$ and inhibitory GABA at delivery might restore physiological parameters in juvenile rodents. To test this hypothesis, pregnant females were treated orally 1 day before delivery with bumetanide (2-2.5 mg/kg in drinking water) and juvenile offspring neurons recorded at P15. Maternal pretreatment of VPA with bumetanide restored control $DF_{GABA}$ values in offsprings at P15 (FIG. 2A, C; table 4), suppressed the excitatory actions of the $GABA_AR$ agonist isoguvacine (FIG. 2B, C) and significantly reduced ongoing activity and frequency of whole-cell recorded glutamatergic sEPSCs (FIG. 3). Therefore, excitatory actions of GABA during delivery produce long term deleterious effects on electrophysiological parameters of VPA juvenile neurons. In VPA rats, GABAergic inputs are excitatory and contribute to hyperexcitability of the network. Bumetanide decreases $[Cl^-]_i$ and consequently reduces contribution of excitatory GABAergic inputs in the overall network activity.

TABLE 4

Depolarizing DF$_{GABA}$ in VPA neurons and restoration by maternal pretreatment with bumetanide (BUM pretreatment).

| | DF$_{GABA}$ (mV), mean ± S.E. |
|---|---|
| Control rats | 3.4 ± 0.6 (n = 22) |
| VPA rats | 10.2 ± 1.0 (n = 25) |
| BUM pretreatment | 0.4 ± 1.1 (n = 58) |
| | VPA vs. BUM pretreatment, P < 0.001 |

Note that DF$_{GABA}$ is depolarizing in neurons recorded at P15 from VPA rodents and control values were restored following maternal pretreatment with bumetanide. The statistics are presented by an unpaired t test.

Example 3

Maternal Pretreatment with Bumetanide Restores Behavior in VPA Rats

Figure 4:
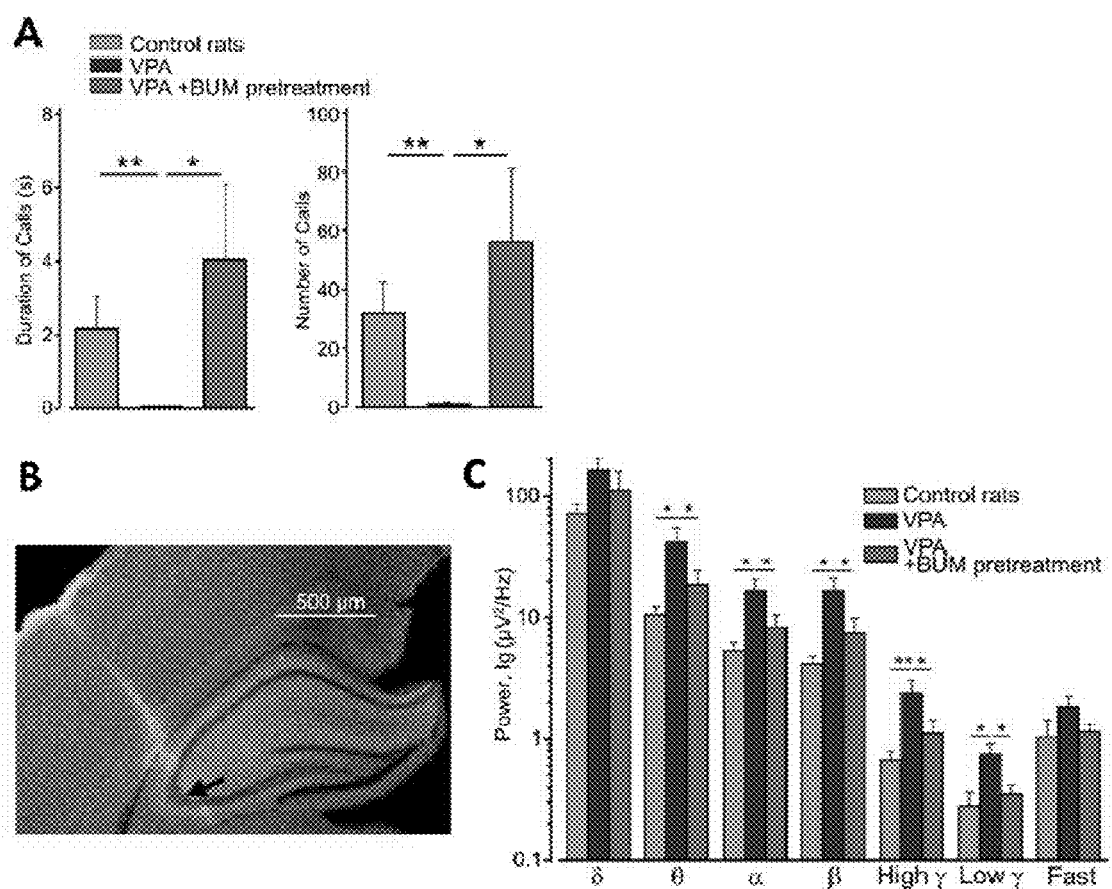
FIG. 4 represents histograms on the effect of maternal pretreatment with Bumetanide in vivo. Isolation-induced Ultrasonic Vocalizations in (A) P4 control (n=18), VPA (n=26) and VPA rats with maternal bumetanide pretreatment (n=20). One-way ANOVA Kruskal-Wallis test, Dunn's Multiple Comparison post-hoc test *$P<0.05$, **$P<0.01$. (B) Electroencephalographic (EEG) recordings in vivo were made in the CA3 area of hippocampus of head-restrained control (n=6), VPA (n=7) and VPA rats with maternal bumetanide pretreatment (n=8) at (P13-P15). (C) A coronal section showing the location of the DiI-labeled recording electrode (arrow). (D) Integral power of δ-(0.5-4 Hz), θ(4-7 Hz), α-(7-12 Hz), β(12-25 Hz), low γ-(25-60 Hz), High γ-(60-120 Hz) band components of EEG revealed by Fourier transform analysis. Control vs. VPA: for θ, α, β and high γ *$P<0.05$, for low γ**$P<0.01$; VPA vs VPA with maternal bumetanide pretreatment for θ, α, β, high and low γ*$P<0.05$.

This led us to test whether maternal bumetanide pretreatment might prevent autistic like behaviors. We found that VPA pups emitted smaller number of calls with a shorter total duration of calls than age matched control P4 pups. Maternal pretreatment with bumetanide rescued this behavioral deficit in offsprings (FIG. 4A, table 5). Therefore, elevated [Cl$^-$]$_i$ levels during delivery are involved in the pathogenesis of autism.

TABLE 5

Altered isolation-induced USVs in 2 models of autism are restored after maternal bumetanide pretreatment.

| P4 | Number of calls | Total duration of calls |
|---|---|---|
| | Isolation-induced USVs mean ± S.E.M | |
| Control rats | 32 ± 11 (n = 18) | 2.2 ± 0.9 (n = 18) |
| Control + BUM pretreatment | 62.6 ± 27.4 (n = 18) | 4.6 ± 2.3 (n = 18) |
| VPA rats | 1 ± 0.5 (n = 26) | 0.04 ± 0.02 (n = 26) |
| VPA + BUM pretreatment | 56 ± 25 (n = 20) | 4 ± 2 (n = 20) |
| | Statistics | |
| Control vs. VPA | P < 0.01 One-way ANOVA Kruskal-Wallis test, Dunn's Multiple Comparison post-hoc test | P < 0.01 One-way ANOVA Kruskal-Wallis test, Dunn's Multiple Comparison post-hoc test |
| VPA vs. VPA + BUM pretreatment | P < 0.05 One-way ANOVA Kruskal-Wallis test, Dunn's Multiple Comparison post-hoc test | P < 0.05 One-way ANOVA Kruskal-Wallis test, Dunn's Multiple Comparison post-hoc test |
| Control vs. Control + BUM pretreatment | n.s. Mann-Whitney test | n.s. Mann-Whitney test |

Control P4 rat pups emitted a higher number of calls with a longer total duration when compared to age matched VPA pups. Maternal pretreatment with bumetanide rescued this behavioral deficit. One-way ANOVA Kruskal-Wallis test, with Dunn's Multiple Comparison post-hoc test, and Mann-Whitney test.

TABLE 6

Electroencephalographic (EEG) recordings in vivo in the CA3 area of hippocampus of head-restrained rats at P13-15.

| Frequency (Hz) | Control | VPA | VPA BUM pretreatment |
|---|---|---|---|
| 0.5-4 | 71.79 ± 13.16 | 164.05 ± 39.44 | 88.53 ± 27.57 |
| 4-7 | 10.49 ± 1.94 | 42.01 ± 12.03 | 15.40 ± 4.25 |
| 7-12 | 5.36 ± 0.85 | 16.52 ± 4.32 | 7.09 ± 1.56 |
| 12-25 | 4.11 ± 0.69 | 16.56 ± 4.78 | 6.35 ± 1.52 |
| 25-60 | 0.67 ± 0.11 | 2.41 ± 0.62 | 0.97 ± 0.20 |
| 60-120 | 0.28 ± 0.08 | 0.74 ± 0.17 | 0.32 ± 0.06 |
| 120-500 | 1.05 ± 0.37 | 1.83 ± 0.42 | 1.18 ± 0.19 |

| Frequency (Hz) | Control vs. VPA | VPA vs. VPA + BUM pretreatment |
|---|---|---|
| 0.3-4 | P = 0.05088 | P = 0.08217 |
| 4-7 | P = 0.01106 | P = 0.01931 |
| 7-12 | P = 0.0124 | P = 0.02122 |
| 12-25 | P = 0.0104 | P = 0.02127 |
| 25-60 | P = 0.0067 | P = 0.01386 |
| 60-120 | P = 0.01445 | P = 0.01635 |
| 120-500 | P = 0.12175 | P = 0.16594 |

Integral power spectra of EEG recordings subdivided by frequency bands for control rats, VPA rats and VPA rats pretreated with bumetanide. Results are mean ± S.E.M. Numbers correspond to FIG. 4C. The statistics are presented by ANOVA followed by post hoc Fisher test.

Finally, as alterations of brain oscillations have been observed in patients with autism, we tested whether similar changes occur in vivo in VPA rats. Using silicon probe recordings in P13-P15 VPA rats, we observed that in contrast to age matched naive rats the EEG recordings in the hippocampal CA3 region were characterized by oscillatory hyperactivity and enhanced power of network oscillations in the entire spectrum of frequencies including gamma but excluding fast ripples and very low (δ) frequencies. Maternal pretreatment with bumetanide abolished hyperactivity and restored physiological values in offsprings (FIG. 4B-C; table 6). Therefore, oscillations in the juvenile brain are strongly dependent on GABA actions during delivery.

The invention claimed is:
1. A method for treating a subject presenting Autistic Syndrome Disorders (ASD), wherein said method comprises the administration of an effective amount of a selective inhibitor of transporter Na—K-2Cl 1 (NKCC1),
   wherein said inhibitor is bumetanide, and
   wherein said subject is a human embryo, a human fetus, a new born child or a young child.
2. The method according to claim 1, wherein the effective amount ranges from about 0.01 mg to about 500 mg.
3. The method according to claim 1, wherein the selective inhibitor of transporter NKCC1 is administered directly to the subject in need thereof by subcutaneous, intramuscular, intravenous, intraocular, transdermal, topical, parenteral, intranasal and oral administration, or injection.

4. The method according to claim 1, wherein the selective inhibitor of transporter NKCC1 is administered perinatally to the subject.

5. The method according to claim 1, wherein the selective inhibitor of transporter NKCC1 is administered to a pregnant woman by subcutaneous, intramuscular, intravenous, intraocular, transdermal, topical, parenteral, intranasal and oral administration, or injection, preferably in utero.

6. The method according to claim 1, wherein the subject suffered from complications delivery.

7. A method for treating a subject at risk of developing ASD, comprising administering an effective amount of a selective inhibitor of NKCC1,
   wherein said inhibitor is bumetanide, and
   wherein said subject is a human embryo, a human fetus, a new born child or a young child.

* * * * *